(12) United States Patent
Zhao et al.

(10) Patent No.: US 11,090,003 B2
(45) Date of Patent: Aug. 17, 2021

(54) SYSTEMS FOR PERSONAL PORTABLE WIRELESS VITAL SIGNS SCANNER

(71) Applicant: HEALTHY.IO LTD., Tel Aviv-Jaffa (IL)

(72) Inventors: Wenyi Zhao, Mountain View, CA (US); Brandon Dennis Woolsey, San Jose, CA (US); Walter De Brouwer, Los Altos, CA (US); Eron Anthony Villarreal, San Jose, CA (US); Whitney Morgan McGowan, San Jose, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 151 days.

(21) Appl. No.: 16/351,523

(22) Filed: Mar. 13, 2019

(65) Prior Publication Data
US 2019/0307400 A1    Oct. 10, 2019

Related U.S. Application Data

(63) Continuation of application No. 14/283,211, filed on May 20, 2014, now abandoned.
(Continued)

(51) Int. Cl.
*A61B 5/00* (2006.01)
*A61B 5/145* (2006.01)
(Continued)

(52) U.S. Cl.
CPC .............. *A61B 5/6826* (2013.01); *A61B 5/01* (2013.01); *A61B 5/021* (2013.01);
(Continued)

(58) Field of Classification Search
None
See application file for complete search history.

(56) References Cited

U.S. PATENT DOCUMENTS 5,921,936 A * 7/1999 Inukai ................ A61B 5/02125
600/485
6,409,675 B1 * 6/2002 Turcott ................ A61B 5/6816
600/508
(Continued)

*Primary Examiner* — Carl H Layno
*Assistant Examiner* — Manolis Pahakis
(74) *Attorney, Agent, or Firm* — Finnegan, Henderson, Farabow, Garrett & Dunner, LLP

(57) ABSTRACT

Methods, systems, and apparatus for periodically and simultaneously scanning for a plurality of vital signs of a user is disclosed. The system includes a personal portable wireless vital signs scanner having a pair of electrodes to form a circuit with a user's body; and a personal wireless multifunction device wirelessly in communication with the personal portable wireless vital signs scanner. The personal portable wireless vital signs scanner includes a processor to concurrently scan for a plurality of vital signs. Some methods include squeezing a personal wireless vital signs scanner between first and second fingers to connect to a first electrode; and pressing the wireless vital signs scanner against a forehead to form a circuit through the body of the user with the personal wireless vital signs scanner. The wireless vital signs scanner may also be pressed against a chest to form a second circuit through the body of the user.

10 Claims, 47 Drawing Sheets

Related U.S. Application Data

(60) Provisional application No. 61/875,681, filed on Sep. 9, 2013.

(51) Int. Cl.
*A61B 5/024* (2006.01)
*A61B 5/01* (2006.01)
*A61B 5/021* (2006.01)
*A61B 5/08* (2006.01)

(52) U.S. Cl.
CPC ........ *A61B 5/02444* (2013.01); *A61B 5/0816* (2013.01); *A61B 5/14542* (2013.01)

(56) References Cited

U.S. PATENT DOCUMENTS

| | | | | |
|---|---|---|---|---|
| 6,491,647 B1* | 12/2002 | Bridger | ................. | A61B 5/021 |
| | | | | 128/900 |
| 8,244,336 B2* | 8/2012 | Wang | .................... | A61B 5/332 |
| | | | | 600/509 |
| 8,782,681 B2* | 7/2014 | Lee | .................... | H04N 21/4756 |
| | | | | 725/10 |
| 9,149,599 B2* | 10/2015 | Walter | ................. | A61M 21/02 |
| 9,782,122 B1* | 10/2017 | Pulliam | ................. | A61B 5/1112 |
| 9,808,206 B1* | 11/2017 | Zhao | .................... | A61B 5/0295 |
| 9,841,812 B2* | 12/2017 | Kitazawa | ............... | A61B 5/389 |
| 2002/0026114 A1* | 2/2002 | Nissila | .................... | A61B 5/25 |
| | | | | 600/384 |
| 2002/0128567 A1* | 9/2002 | Lange | ................. | A61B 5/4824 |
| | | | | 600/544 |
| 2002/0165462 A1* | 11/2002 | Westbrook | ......... | A61B 5/14552 |
| | | | | 600/529 |
| 2003/0107487 A1* | 6/2003 | Korman | ............... | A61B 5/0205 |
| | | | | 340/573.1 |
| 2004/0167408 A1* | 8/2004 | Ashida | .................... | G16H 10/60 |
| | | | | 600/485 |
| 2004/0193068 A1* | 9/2004 | Burton | ................. | A61B 5/4812 |
| | | | | 600/544 |
| 2005/0027203 A1* | 2/2005 | Umeda | ................. | A61B 5/332 |
| | | | | 600/509 |
| 2007/0100219 A1* | 5/2007 | Sweitzer | ............ | A61B 5/14551 |
| | | | | 600/323 |
| 2007/0276632 A1* | 11/2007 | Banet | ................... | A61B 5/0004 |
| | | | | 702/187 |
| 2007/0299322 A1* | 12/2007 | Miyajima | ........... | H04M 1/0202 |
| | | | | 600/301 |
| 2008/0091090 A1* | 4/2008 | Guillory | .............. | A61B 5/6814 |
| | | | | 600/301 |
| 2008/0221413 A1* | 9/2008 | Hoarau | ................ | A61B 5/6814 |
| | | | | 600/310 |
| 2008/0243020 A1* | 10/2008 | Chou | .................... | G16H 40/63 |
| | | | | 600/538 |
| 2009/0171170 A1* | 7/2009 | Li | ....................... | A61B 5/14551 |
| | | | | 600/301 |
| 2010/0191074 A1* | 7/2010 | Chou | .................... | G16H 40/67 |
| | | | | 600/301 |
| 2011/0015496 A1* | 1/2011 | Sherman | ................ | A61B 5/332 |
| | | | | 600/301 |
| 2011/0145012 A1* | 6/2011 | Nightingale | ........... | G16H 20/10 |
| | | | | 705/3 |
| 2011/0191116 A1* | 8/2011 | Loser | .................... | G16H 40/63 |
| | | | | 705/2 |
| 2012/0022385 A1* | 1/2012 | Shimuta | ................ | A61B 5/332 |
| | | | | 600/509 |
| 2012/0150545 A1* | 6/2012 | Simon | .................... | A61B 5/162 |
| | | | | 704/270 |
| 2012/0245482 A1* | 9/2012 | Bolser | .................... | A61B 5/296 |
| | | | | 600/546 |
| 2013/0116520 A1* | 5/2013 | Roham | ................ | A61B 5/6833 |
| | | | | 600/324 |
| 2013/0276785 A1* | 10/2013 | Melker | .................... | G16H 20/17 |
| | | | | 128/204.23 |
| 2014/0051941 A1* | 2/2014 | Messerschmidt | .. | A61B 5/02416 |
| | | | | 600/301 |
| 2015/0148646 A1* | 5/2015 | Park | ....................... | H05K 1/115 |
| | | | | 600/391 |
| 2015/0313484 A1* | 11/2015 | Burg | ....................... | A61B 5/021 |
| | | | | 600/301 |
| 2015/0313498 A1* | 11/2015 | Coleman | .............. | A61B 5/6803 |
| | | | | 600/383 |
| 2015/0335283 A1* | 11/2015 | Fish | .................... | A61B 5/02444 |
| | | | | 600/324 |
| 2016/0000379 A1* | 1/2016 | Pougatchev | ........... | A61B 5/352 |
| | | | | 600/479 |

* cited by examiner

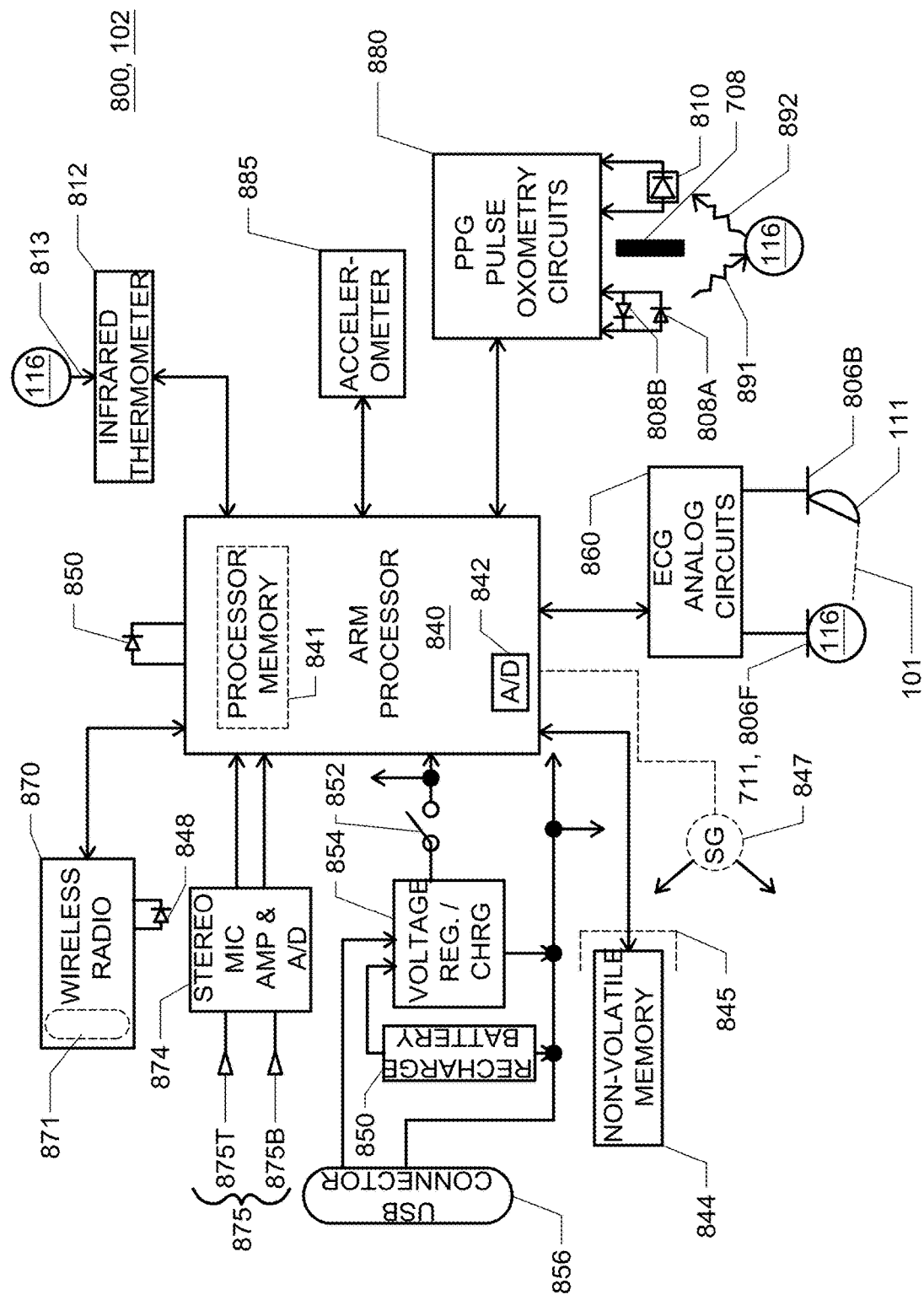

SYSTEMS FOR PERSONAL PORTABLE WIRELESS VITAL SIGNS SCANNER

CROSS REFERENCE TO RELATED APPLICATIONS

This non-provisional patent application is a continuation and claims priority to U.S. patent application Ser. No. 14/283,211, now abandoned; SYSTEMS FOR PERSONAL PORTABLE WIRELESS VITAL SIGNS SCANNER filed by inventors Wenyi Zhao et al., on May 20, 2014. U.S. patent application Ser. No. 14/283,211 claims priority to provisional patent application No. 61/875,681; entitled SYSTEMS, METHODS, AND APPARATUS FOR PERSONAL PORTABLE WIRELESS VITAL SIGNS SCANNER filed by inventors Wenyi Zhao et al., on Sep. 9, 2013; incorporated herein by reference.

FIELD OF THE INVENTION

This invention generally relates to vital signs scanning by a portable device with multiple integrated sensors.

BACKGROUND OF THE INVENTION

Healthcare is a key element of any modern society. Over the years, it has brought people the benefit of the latest technological breakthroughs that are safeguarded by well-established regulatory process. The practice of medical practitioners has also evolved into highly specialized fields and subfields. One of the most important aspects of medicine is preventive care. A significant portion of healthcare costs could be reduced if ailments are diagnosed early. Yet many of the tools to diagnose early symptoms are unavailable to the average consumer.

Vital signs of one's body, such as temperature for example, form the base map of ones health. Fluctuations in our vital signs may be predictive of undiagnosed ailments. It's important to have easy access to their vital signs as frequently as needed. Yet the average consumer has no easy method of obtaining many of their vital signs without visiting a hospital or clinic. One of the easiest-to-measure vital signs is body temperature. Consumers are able to measure body temperature at home with an inexpensive home thermometer. However the average consumer still does not have easy access to devices for measuring the other important vital signs of ones body, such as blood oxygenation or blood pressure for example. The technology is available to measure the important vital signs, but typically limited to clinics and hospitals.

Consumers do not have a way to measure all of their important vital signs at home. Consumers cannot visit their physician five or more times a day to constantly monitor their vital signs. This has put the average consumer with a medical condition into a difficult situation, where they do not know what to do with their condition when they need vital signs information while at home or traveling. The few options the average consumer has with an unknown medical condition include staying calm and doing nothing, calling their primary care providers (PCP) to get an appointment, or visiting an emergency room (ER) and waiting for hours.

Even if the consumer opted to do one of the latter options, the PCP or ER may not be able to provide personalized advice without knowing the specifics about their patients. The physician may have some idea about one's health condition based on an annual exam but the data may be outdated and useless with a current medical condition.

As a result, the average consumer may not receive the best medical care due to the lack of information. And together, with PCPs, we also manage to add more cost to the healthcare system that is already very expensive as people live longer.

The problem, simply put, is that consumer access to basic health care is rather limited. It is desirable to improve the quality and access to basic health care for average consumers.

SUMMARY OF THE INVENTION

The embodiments of the invention are best summarized by the claims below. Insofar as a summary is required, one embodiment of the invention that is disclosed is a portable vital signs scanner with integrated vital signs sensors.

BRIEF DESCRIPTION OF THE DRAWINGS

These and other features, aspects, and advantages of the present disclosure will now be described with reference to the drawings of embodiments, which embodiments are intended to illustrate and not to limit the disclosure, as are described in varying degrees of detail below.

FIG. 8A illustrates a functional block diagram of electronic circuitry within the exemplary portable wireless vital signs scanner.

FIGS. 10A-19A, 10B-19B, 10C-19C illustrate various views of the vital signs scanner and housing therefor.

DETAILED DESCRIPTION

Figure 1A:
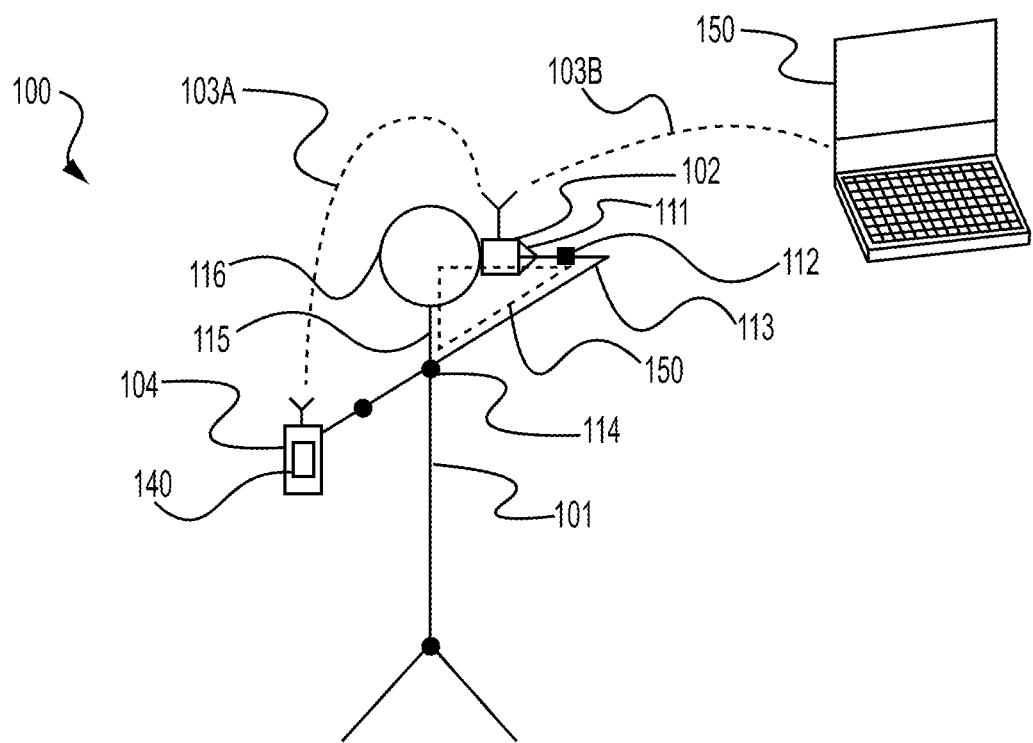
FIG. 1A is a diagram illustrating an exemplary vital signs scanning system with the scanner held at the forehead/temple.

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more particular embodiments may also be included in combination with another embodiment even though not expressly shown and described in that specific combination.

For purpose of efficiency, reference numbers may be repeated between the figures where they are intended to represent similar features between otherwise varied embodiments, though those features may also incorporate certain differences between embodiments if and to the extent specified as such or otherwise apparent to one of ordinary skill (such as differences clearly shown between them in the respective figures).

It is desirable for consumers to take greater control of their own basic health and work with their primary care providers (PCPs) to provide personalized healthcare. Some embodiments of the invention provide a consumer device that is small enough to be carried in a pocket or purse with which effortless vital signs scans can be performed, anytime, anywhere. The consumer device, referred to as a vital signs scanner, can transfer the vital signs results to a portable wireless multifunction device, such as a smartphone, for storage and display to a user over time to illustrate health trends. The vital signs scanner allows consumers to take greater control of their own basic health and work with PCPs to provide personalized healthcare.

The vital signs scanner allows users to efficiently measure multiple vital signs simultaneously. Vital signs scanning with the vital signs scanner is quick and easy and very convenient in that it can simultaneously capture a plurality of vita signs data with one scanning session (one or two vital signs scans) at a given time and date. The vital signs data is transferred to a user's own portable multifunction touch screen device, e.g. a smart phone. The portable multifunction device, with the assistance of vital signs scanning software, displays the scanning results in an intuitive user interface that is simple to understand.

The vital signs scanning device provides a method of vital signs scanning to help solve the missing information link so a user can take control of managing his/her own health. In addition to providing vital signs scanning, the vital signs scanner and system also stores the users vital signs measurements and trends over time of a day and date. The vital signs scanner and system provides easy access (almost anywhere at anytime) to important vital signs measurements such as blood oxygenation, blood pressure, heart rate, etc. The vital signs scanner and system can help share up-to-date vital signs data with a user's PCP for better diagnosis of medical conditions. Perhaps even more importantly, sharing of history and trends of vital signs data before and after an ailment with the user's PCP can provide clues to its cause and not just indicate the symptoms.

The personal wireless vital signs scanner combines aesthetic design with functionality. The personal wireless vital signs scanner is light weight and easily fits into one hand. The personal wireless vital signs scanner can be held and operated with just two fingers of one hand. The user's other hand is free to hold a smartphone with a vital signs scanning application running to control the vital signs scanning process and view the scanning results. Vital signs data of a users body can change at different times of each day. The personal wireless vital signs scanner is so small, light, and esthetically pleasing that a user may desire to take it with them to perform a plurality of vital signs scans at different times throughout his/her day over a plurality of days.

A portable vital signs scanner and system may prove to be useful for healthcare professionals as well. For example, patients could scan for their own vital signs themselves in a busy hospital, clinic or doctors office, rather than wait in long lines just to get a simple checkup before seeing the doctor. The patients scans are then uploaded to a server at the hospital, clinic, or office. With these self-obtained vital signs scans of patients being uploaded to a server, medical assistants and nurses, ordinarily checking for vital signs, can better spend their time curing the ailments of the patients.

The self-obtained vital signs scans of patients may also serve to triage the patients that are waiting for medical care. For example, a self-obtained vital signs scan of a patient indicating an elevated or irregular heart rate may signal hospital staff to attend to this patient immediately or at least a higher priority in a queue of patients. In this manner, the self-obtained vital signs scans of patients provide a clinic staff with a sense of the severity of the condition of patients waiting and can make appropriate schedule priority adjustments, if needed.

Referring now to FIG. 1A, a diagram illustrating a vital signs scanning system 100 is shown. The scanning system 100 includes a portable wireless vital signs scanner 102 and a portable wireless multifunction device 104 in wireless communication with each other over a wireless communication channel 103A. The vital signs scanner 102 includes a plurality of sensors designed to read vital signs from a user's body 101. An instance or snap shot of vital signs, such as temperature, heart rate, blood oxygenation or SpO2, ECG (electrocardiogram), and possibly stress levels, all synchronously measured, can be reported to the device 104 by the scanner 102 in less than a minute. Integration of multiple sensors and scan quality algorithms make it possible to monitor the quality of the scanning process and then provide intuitive user feedback to control the interactive scanning process, to make a great user experience in the vital signs scanning process.

The wireless vital signs scanner 102 may perform vital signs scans and display the results in under a minute. Generally scans may be completed in approximately ten seconds. The length of a scanning session may depend on the user's ability to correctly utilize the scanner 102. For example, if the user moves too much during the scanning session, the session will last longer as the device 104 prompts the user to remain still.

Different types of scans may also take different lengths of time. For example, in a standard ten second head scan where the scanner is held against a user's forehead or temple, temperature, SpO2, ECG, heart rate, blood pressure may be measured. For a 30 second extended head scan, vital signs such as blood pressure and heart rate variability (related to emotional stress) may be captured. For a thirty second chest scan from a user's chest, respiration rate and body sounds may be measured or collected. In any case, the scanning sessions are still short and convenient.

Short scanning sessions have several advantages. A short scanning session allows a user to take a quick break from their daily activities to perform a scan anywhere and at any time. The ease and rapidness of performing a vital signs scan will encourage users to perform the scan multiple times a day, providing more complete and accurate trending data. The invention provides a consumer oriented scanner that a user can use anytime anywhere to obtain multiple vital sign measurements in seconds.

Short scanning sessions also conserve power. With ten second scans, the scanner is designed to last for one week of normal usage with one full battery charge. If the power is on for a total of about 30 seconds for each scan, then total power-on time for each day is less than one hour with 100 scans per day. The scanner 102 may operate for a week at a time between battery recharging sessions.

Scanner 102 is an elegant consumer device that is portable. Unlike other vital sign monitors, scanner 102 does not need to be worn. Scanner 102 is perhaps the smallest consumer device that can measure multiple vital signs simultaneously. Measuring approximately 60 mm in diameter and 18 mm high, the scanner 102 can be easily places in a pocket or purse for use at any time convenient to the user. At any time the user has a moment to spare, the scanner 102 may be used to obtain multiple vital sign measurements by simply finger-holding it against the user's forehead/temple and/or chest.

Using a multifunction device 104 to display the vital signs scanning results allows the scanner 102 to maintain a compact size and minimalist form. Multifunction device 104 may be any portable wireless multifunction device such as a smartphone, tablet PC, or the so called smart watches. Generally these devices are pre-owned and already available to the average consumer, so utilizing the display capabilities of multifunction device 104 does not detract from the portability of the invention. The ubiquity of smartphones also means that the average consumer does not need to pay more for a dedicated display device. Combining the vital signs scanner 102 with, a smartphone that a user already has, allows one to take control and greater responsibility for his/her health without sacrificing valuable time and money.

To display the vital signs scanning results, the portable wireless digital device 104 executes a vital signs scanning software application 140. The instructions of the vital signs scanning software application 140 are executable with the operating system, (e.g., Android and iOS), of the multifunction device 104. Once the software application is active, the user may power up the vital signs scanner 102. Upon power up, the vital signs scanner 102 is paired with the portable wireless digital device 104 to form the communication channel 103A between them. Accordingly, each of the scanner 102 and multifunction device 104 has a compatible wireless radio to form a compatible wireless communication channel. In one embodiment, the communication channel 103A is a Bluetooth version 4, a smart low energy (LE) supported channel that each wireless radio supports. The vital signs scanner 102 sends the vital sign information wirelessly to the portable wireless multifunction scanner 102 over the wireless communication channel 103A for storage and further analysis.

With the communication channel 103A available, the vital signs scanner 102 is pressed against a user's forehead/temple. The forehead/temple is identified as the single place with enough blood vessels and thin skin so that temperature, pulse oximetry and ECG can be obtained in sync and time-stamped. A scanning button is pressed on the user interface of the application 140 of the portable wireless multifunction device 104 to start the scanner 102 scanning for vital signs information of the user. After scanning for approximately 10 seconds or less, the vital signs scanner 102 sends the vital sign information wirelessly to the portable wireless multifunction device 102. The multifunction device 104 may display the results of the scan on a touchscreen display.

The vital signs scanner 102 is used periodically to scan for vital signs each day. Statistical information regarding a plurality of scans each day over a plurality of days can be generated and displayed on the touchscreen display device of the device 140. The vital signs scanning software application 140 informs a user of how those vital sign measurements may change during times of a day and over a plurality of days.

An important aspect of the invention is the quality of the scanning results. To optimize the scanning session results, the scanner 102 is designed to be easy to use to minimize user error. Similarly, the scanning software application is intuitive and easy to use. With minimal instruction, an average user can generate medical grade vital signs scans within minutes of using the invention for the first time.

To further optimize scanning results, scan quality algorithm monitor the vita signs scanning process and provides feedback (visual and/or audible) to the user through the multifunction device 104, and/or alternatively an optional sound generator (see audible sound generator 847 in FIGS. 8A-8B) in the scanner 102. The user feedback may help the user to perform a better vital signs scan with the wireless vital signs scanner and acquire good quality vital signs measurements.

Integration of multiple sensors allows for synergistic accuracy of vital signs scans. For example, integration of an accelerometer enables motion detection that is often associated with poor signals of pulse oximetry and ECG. In another example, abnormal signals of both pulse oximetry and ECG suggest the device is not held against the body properly. This can be further confirmed by comparing the surface temperature and ambient temperature of the sensor when not in touch with the user. Quality checking of individual vital sign measurements is based on fusion of multiple sensors, including a motion sensor, such as an accelerometer. Signal quality may be checked based on dynamic range detection and thresholding, for example. To make the process more robust, known signal processing techniques, such as envelope detection, can be applied to the raw signals from the sensors as a preprocessing or screening step. Quality checking of raw sensor signals from the sensors makes sensor data fusion more robust by rejecting bad signals. Thus, fusing results of multiple sensors can provide better individual measurements of each vital sign.

The intuitive scanning user interface (UI) is designed, in combination with scan quality algorithms and the device's self-diagnostic capability, to help users to finish a vital signs scan successfully. There is the quality indicator from the quality algorithm, the progress bar, and texts that provides feedback to the user to ensure a successful scanning session. For example, suggestions to "hold still" or "hold device to your forehead" may prompt the user to correct his/her poor scanning behavior.

The scanning system 100 is user friendly so that it can be used multiple times during the day to obtain data about a user's body 101. One person or one family can exclusively use the scanning system 100 and scanner 102 at home as a personal vital signs scanner. In this manner, a measure of one's personal health and medical data can be obtained right at home with the scanning system 100 without seeing a doctor or being admitted to a hospital. Each scan only lasts approximately ten to thirty seconds and obtains multiple vital sings measurements so users can take the scan repeatedly throughout the day without being inconvenienced.

The scanning system 100 can be used to personally analyze and track one's own vital signs to see various trends over time. Accordingly, the vital signs data can be accumulated over a plurality of days and a plurality of scans at various times each day, then stored in non-volatile manner with the device 104 so the data does not get lost. The vital signs data can also be backed up to a computer, a storage device, or storage server so it is not lost if the device 104 is lost or stolen. The storage server having greater storage may also be used to accumulate ones user data over a plurality of years when the device 104 is limited by its built-in storage capacity.

In operation, the vital signs scanning system 100 forms an electrical circuit 150 with the user's body 101. The circuit 150 is formed between first and second electrodes of the portable wireless vital signs scanner 102. From a first electrode of the scanner 102, the circuit 150 is made with the fingers 111, the hand 112, the arm 113, the chest 114, the neck 115, and the head 116 of the user's body 101 to a front electrode. Preferably, the portable wireless vital signs scanner 102 forms an electrical connection to the forehead/temple portion of the head 116 of a user's body 101. Fingers 111 not only serve to hold the scanner 102, but also as one contact point for one-lead ECG (the other one-lead ECG contact point is forehead/temple). Preferably the thumb finger 111 in one embodiment and the index finger in another embodiment forms an electrical connection with the portable wireless vital signs scanner 102.

The vital signs scanning system 100 may optionally include a personal computer 150 in wireless communication with the portable wireless vital signs scanner 102 over an alternate or additional wireless communication channel 103B.

Figure 1B:
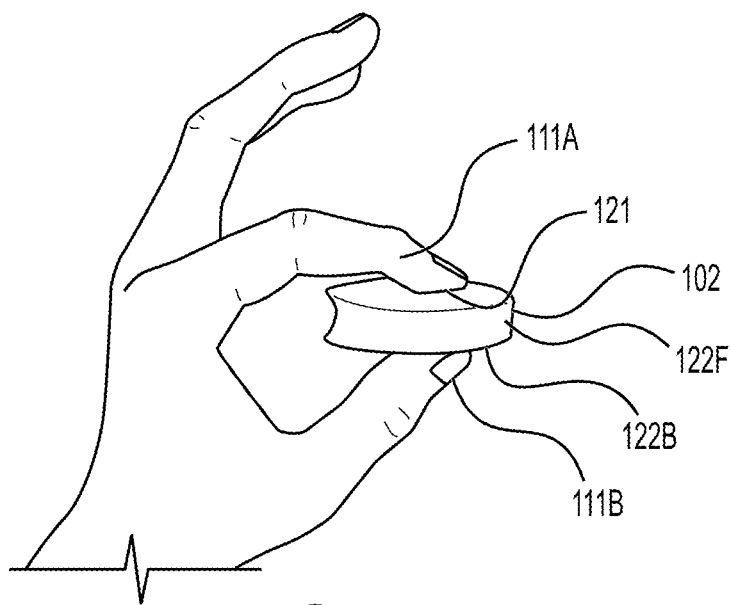
FIG. 1B is a perspective view of a user squeezing the exemplary vital signs scanner.

Referring now to FIG. 1B, a perspective view of a user's fingers 111A-111B squeezing the vital signs scanner 102 is shown. The vital signs scanner 102 is squeezed between the user's fingers to form at least one electrical connection. The front side sensors and a front electrode in the vital signs scanner 102 are then pressed against the user's forehead/temple to form an addition electrical connection. The small size 60 mm×60 mm×18 mm allows the scanner 102 to be held by just two fingers of one hand. At a weight of approximately 60 g, the scanner 102 may be used by just about any person, from a child to the very elderly. Finger-held form-factor, ten to thirty seconds per scan, scan quality algorithm with feedback and an intuitive scanning user interface on a personal portable multifunction device, all help make vital signs scanning fast and easy while producing quality results.

Preferably, the scanner 102 is held between the thumb 111B and forefinger 111A of the user's left hand. The forefinger 111A may also rest over a sensor 121 and forms an electrical connection to an electrode around the sensor in one embodiment. In another embodiment, the thumb finger 111B makes contact with a bottom electrode 122B. The thumb of the left hand couples to the bottom electrical contact (electrode) on the bottom-housing portion of the scanner.

The forefinger makes contact with a rectangular glass plate over an oximeter sensor 121 in one embodiment. In another embodiment, the oximeter sensor 121 is moved to the front side of the vital signs scanner 102 so that extraneous light is less likely to interfere with the its readings.

A front side electrode 122F makes contact with the user's forehead or temple, when it is pressed up against his/her head. An infrared (IR) thermometer sensor is combined with the front side electrode 122F. The IR thermometer sensor makes temperature readings at the user's forehead/temple. An oximeter sensor may also be located near the front side electrode 122F.

With the thumb finger 111B in contact with the bottom electrode 122B, a circuit may be formed through the finger and the hand of the user and a portion of his body back to the front side electrode 122F in the vital signs scanner 102. Once proper placement of scanner 102 is made, a scan button is selected in the software application 140 of the device 104 to command the scanner to scan the vital signs from the user's body and forward them to multifunction device 104.

Figure 1C:
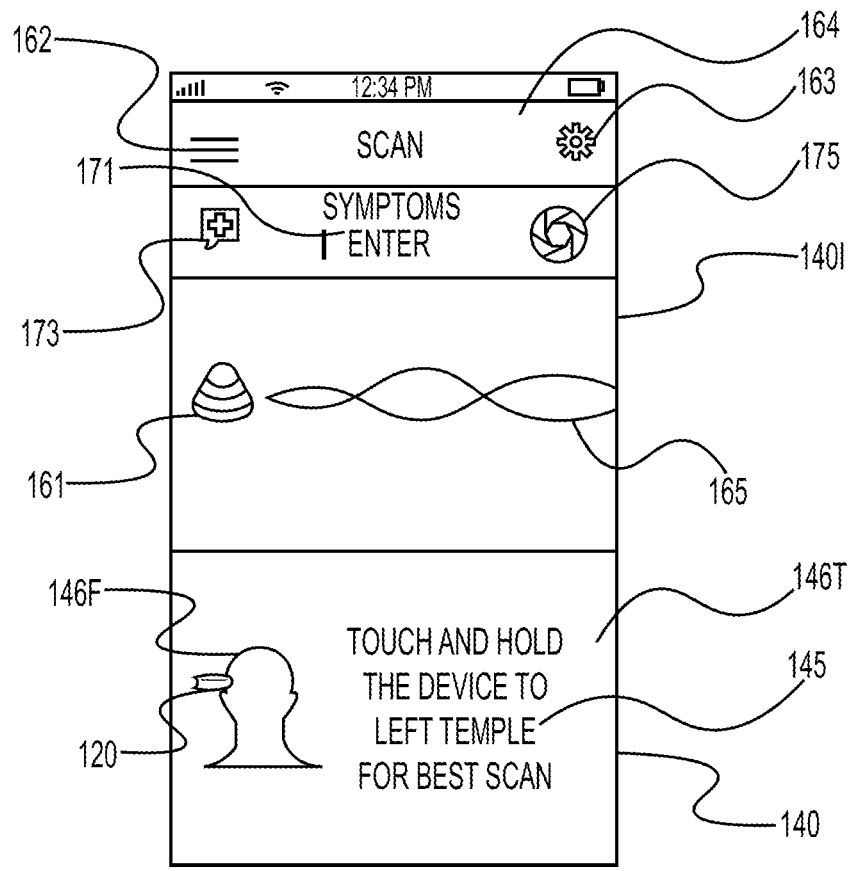
FIG. 1C is a diagram illustrating an exemplary scan screen of a vital signs user interface displayed by a portable wireless multifunctional device.

Referring now to FIG. 1C, in an exemplary initial window 140I of the vital signs scanning application 140 as illustrated, the initial window 140I includes an instruction area 145 with instruction text 146T and an instruction FIG. 146F to show the user how the vital signs scanner 120 is utilized. As indicated by the instruction text 146T, the user is to hold the device to the user's left temple for the best scan.

The initial window 140I further includes a scan button 161, a scan settings button 164, and a scan preferences icon button 163. The scan button 161 may be a button or a swipe to take the user to the next screen or scanning window. The scan preferences button 163 can set up options that are available in the vital signs scanning application 140.

The vital signs scanning application 140 includes an option to enter the user's symptoms by selecting the symptoms entry button 171. A photo may also be taken of the medical condition of a user by use of a camera in the device 104 and a photo entry button 175. Additionally, a user may add a note using an add note button 173.

The status of the scanner 102, such as powered on/off, blue tooth connection, battery charge status, and/or ready to scan, may also be displayed in one or more of the user interface windows of the vital signs scanning application 140.

The scanner 102 can collect a diverse set of physiological information (e.g., vital signs) during one or two acquisition periods totaling approximately sixty seconds (head scan, extended head scan, and/or chest scan).

Figure 1D:
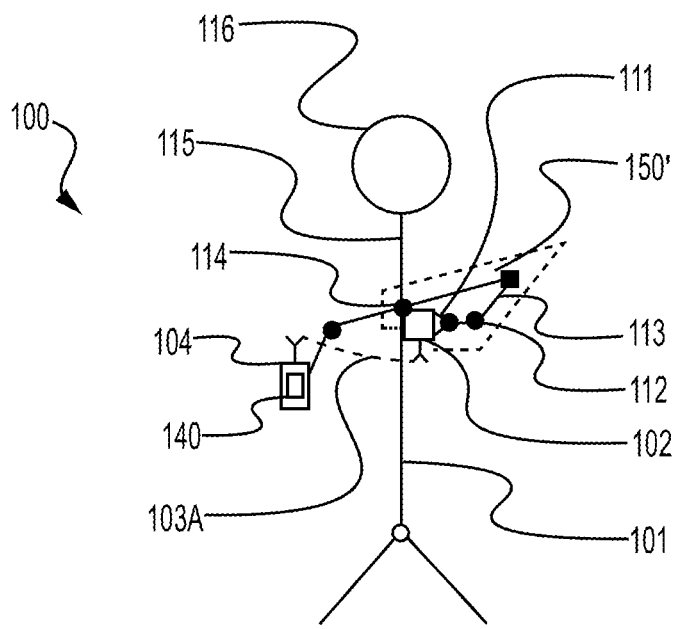
FIG. 1D is another diagram illustrating an exemplary vital signs scanning system with the scanner held at the chest position.

Referring now to FIG. 1D, a diagram of an exemplary vital signs scanning system with the scanner held at the chest position is illustrated. In this embodiment, vital signs are first acquired from a first 10-second scan at the forehead/temple as shown in FIG. 1A. Vital signs may the further be acquired by secondary scans. A longer or extended scan at the forehead/temple with the scanner 102 may be used to capture sensor data as shown in FIG. 1A during a second scanning period. Alternatively or additionally, a subsequent scan conducted near the chest of the user may be performed with the scanner 102 during another scanning period, such as shown in FIG. 1D.

A secondary extended scan at the forehead may be over a range of time from about thirty seconds up to a minute so that measures of heart rate variability and respiration rate may be obtained. The secondary extended scan at the forehead/temple can also provide for a more robust and accurate measurement of blood pressure. In terms of using the scanner, the primary and secondary scans at the forehead may occur in one single scan (e.g., 10-second or 30-second) or two separate scans (e.g., a first at 10 seconds and then a second at 30 seconds).

The secondary extended scan near the chest, a chest scan, is mainly to capture vital signs of respiration rate and additional physiological information from the captured body sounds. The vital signs scanned at the chest area may also include heart rate variability. The secondary extended scan near the chest may last for a period from thirty seconds to a minute. The vital signs scanning application executed on the multifunction device 104 may prompt the user for one or both scan locations.

Figure 3A:
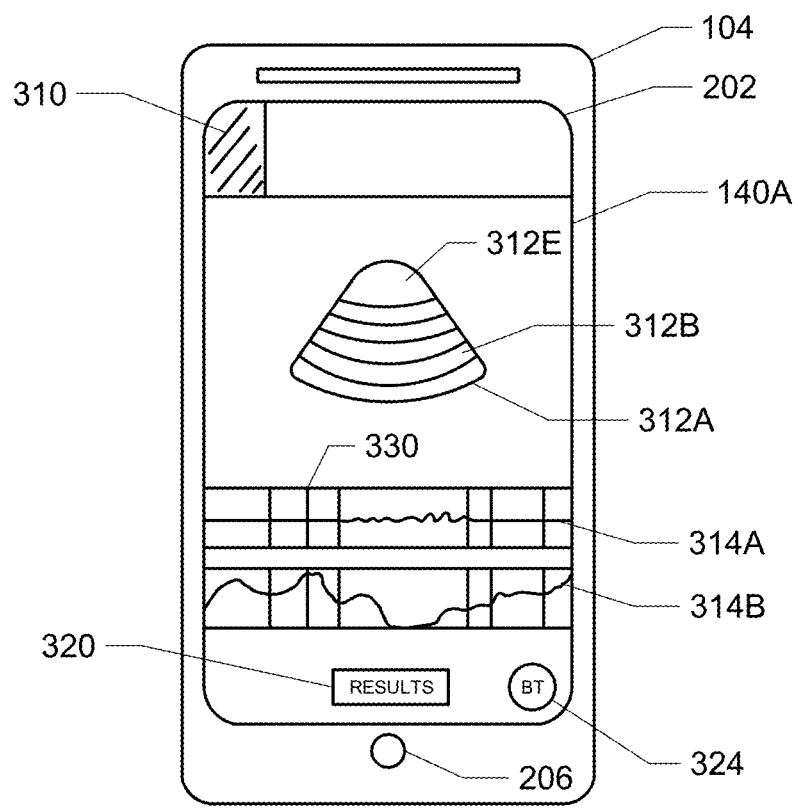
FIG. 3A is an exemplary scanning window displayed on the portable wireless device.
Figure 3B:
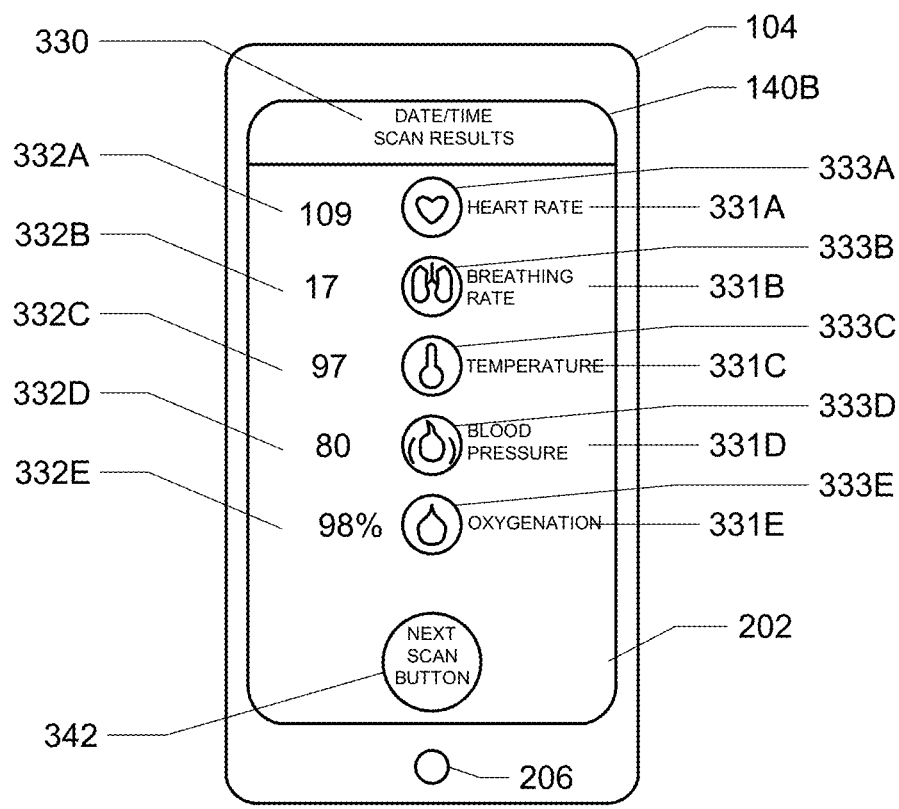
FIG. 3B-3C illustrates an exemplary window generated by the vital signs scanning application on the portable wireless device that displays the user's vital signs.
Figure 3C:
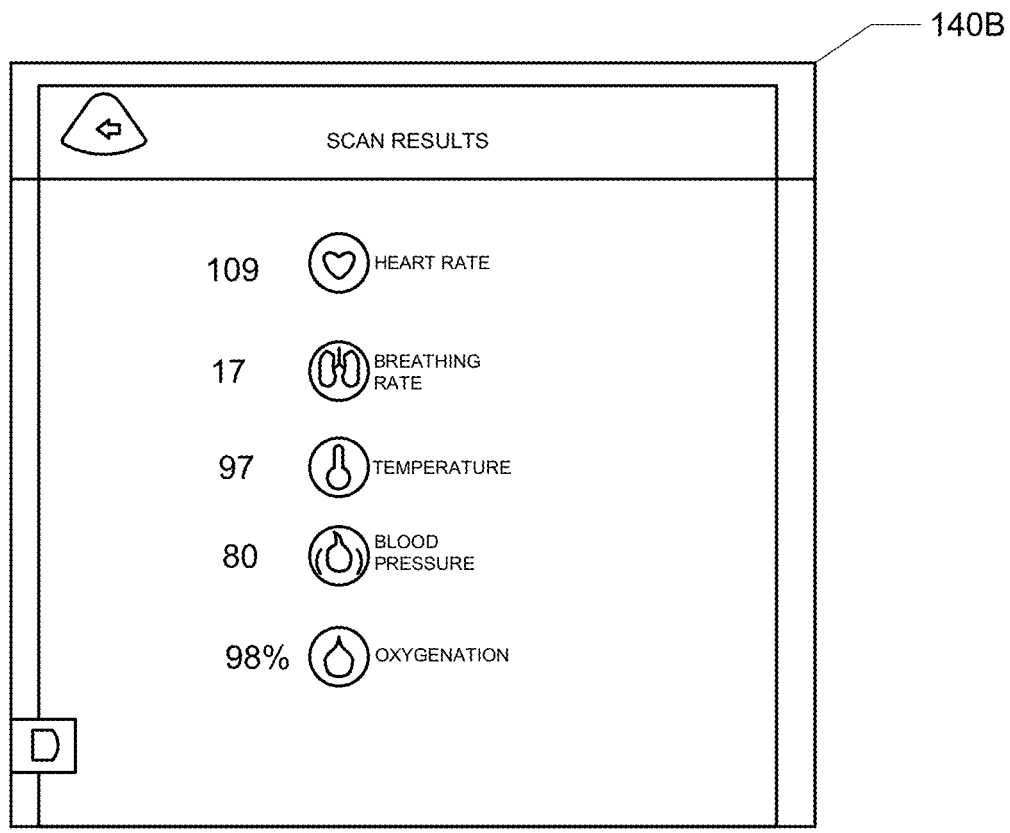
Figure 3D:
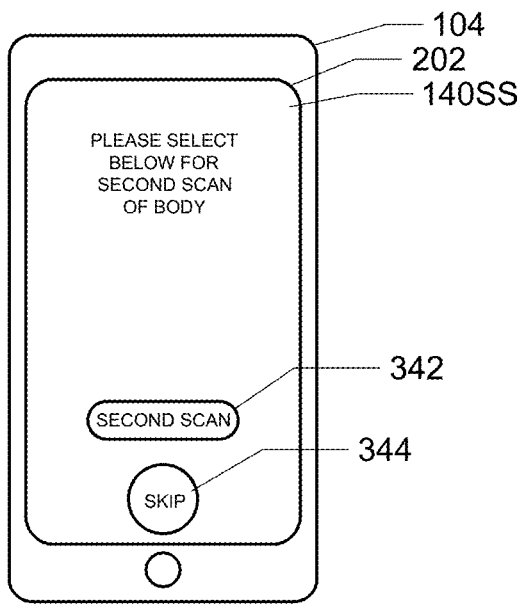
FIG. 3D illustrates an exemplary second scan selection window of the vital signs scanning application on the portable wireless device.

In FIG. 3D, an exemplary secondary scan selection window 140S is illustrated being displayed in the touchscreen of the device 104. The exemplary secondary scan selection window 140S displays instructional text 341 to select user interface buttons displayed below to selectively perform a second and/or third scan or not. A second or third scan button 342 may be selected or a finger swipe gesture may alternatively be used to select to perform the second scan or the third scan at the chest of the user. If only the first scan was desired, a skip button 344 may be selected to avoid the secondary scans. This may be because its inconvenient due to timing or to perform against ones chest with the vital signs scanner, such as when it is inconvenient to do so in public.

Figure 1E:
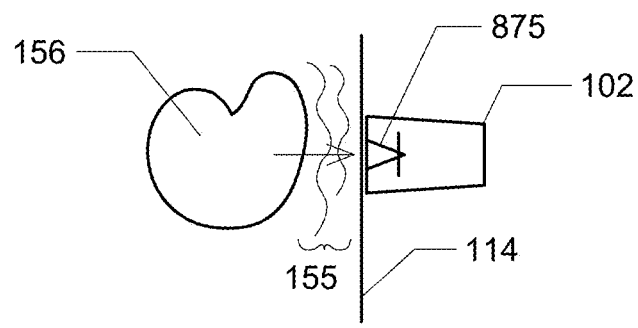
FIGS. 1E-1F are diagrams illustrating how microphones of the exemplary vital signs scanner can capture body sounds, such as from a user's heart or lung.
Figure 1F:
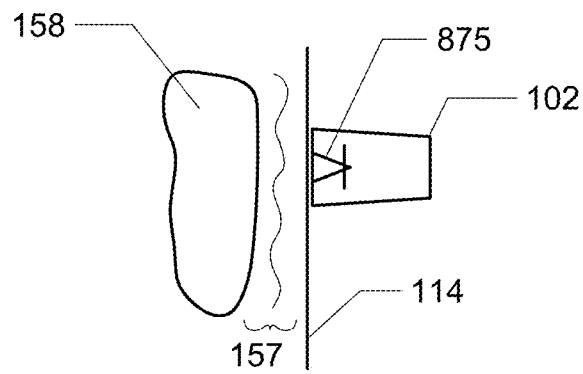

As mentioned herein, a chest scan may be performed with the scanner 102 as shown by FIGS. 1D, 1E, and 1F, for example. In FIG. 1D, a second circuit 150' may be formed with the users body 101 between the electrodes of the scanner 102. The second circuit 150' in this case includes the chest 114, the arm 113, the hand 112, and the finger 111 of the user.

Figure 1G:
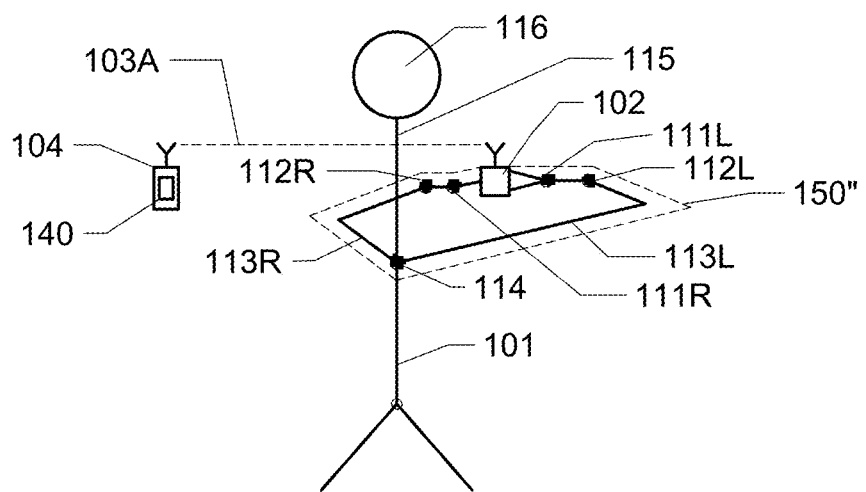
FIG. 1G is another diagram illustrating an exemplary vital signs scanning system with the scanner held in fingers of each hand.

In an alternate embodiment, another circuit 150" may be formed with the users body between the electrodes of the scanner 102 while the device 104 is nearby. This alternate circuit 150" is formed by fingers on different hands coupling to the electrodes of the scanner 102. A left finger 111L may couple to a bottom or top electrode in the scanner 102. A right finger 111R may be coupled to the front electrode of the scanner 102. From a left finger 111L in a left hand 112L of the user, the circuit in the body includes, the left finger 111L, the left hand 112L, the left arm 113L, the chest 114, the right arm 113R, the right hand 112R, and a right finger 111R, such as shown in FIG. 1G, to complete a circuit with the scanner 102.

In either case, the ECG circuitry in the scanner 102 may then obtain further data regarding heart activity of the user that can be combined/fused with the heart activity data of a first scan, to improve the measure of vital signs of heart activity. The vital sign measures of heart activity may then be sent to the device 104 for display to the user on its built-in touchscreen display.

Temperature of the body adjacent the user's chest 114, if reliable, may also be used by the scanner to improve scanning results of temperature. Temperature at the user's finger 111R, if reliable, may also be used by the scanner to improve scanning results of temperature.

With the scanner against the users chest, an accelerometer (see accelerometer 885 in FIGS. 8A-8B) in the scanner 102 may be used to capture movement of the chest as a measure of respiration rate. The vital signs data from these measures are computed by the processor 840 and then sent to the device 140.

FIGS. 1E and 1F illustrate the use of the microphones 875 in the scanner 102 to capture body sounds around the chest 114, such as heart sounds 155 and lung or breathing sounds 157. These body sounds may be recorded to capture another symptom of a user's medical condition. Body sounds that are captured may also be used to judge the quality of the vital signs scanning process. The recorded body sounds may be stored locally in the memory of the scanner and/or sent to the device 140 for storage with the vital signs data of the same time and date.

Figure 2A:
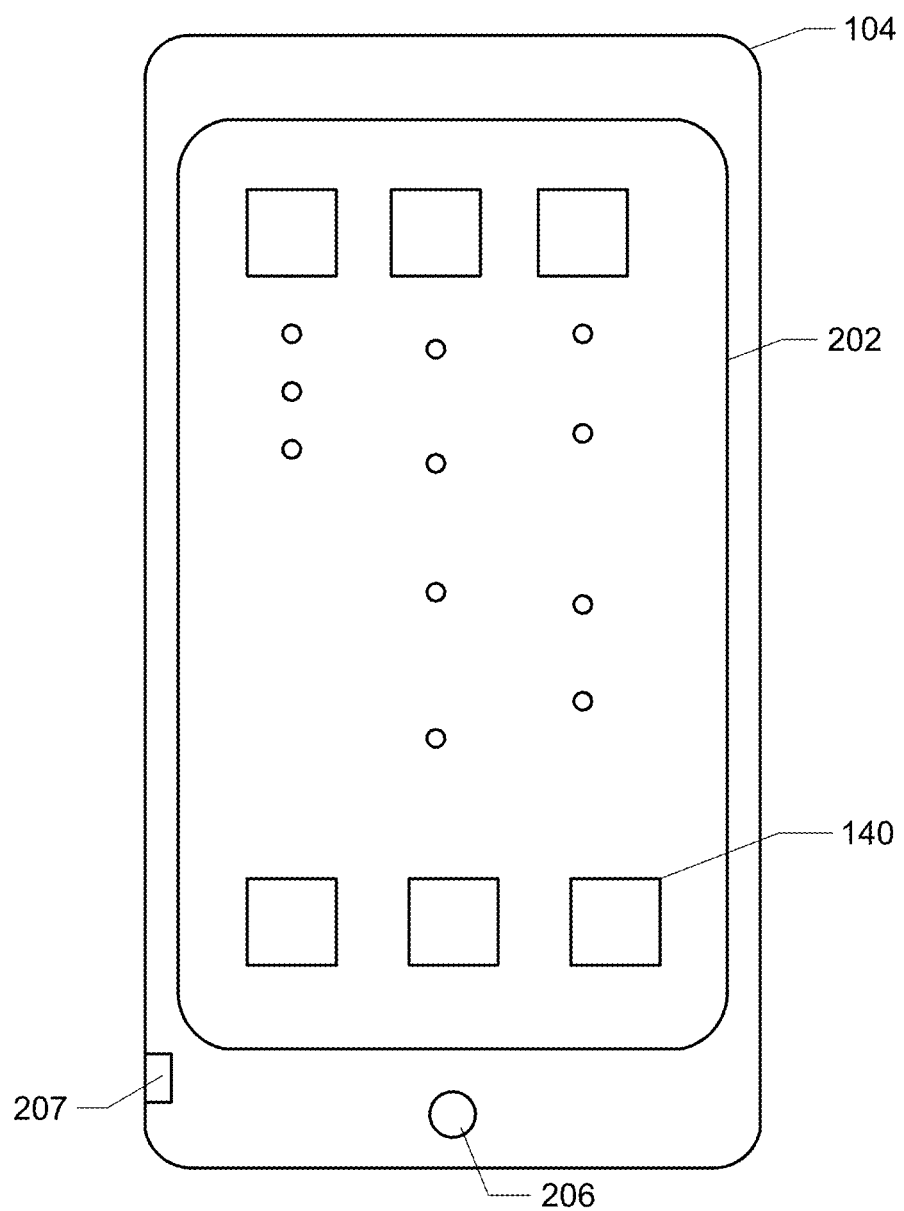
FIG. 2A illustrates an exemplary portable wireless multifunction device to execute the vital signs scanning application.

Referring now to FIG. 2A, a portable wireless multifunction device 104 is illustrated that can execute the vital signs scanning application 140. The portable wireless multifunction device 104 includes a text screen 202, at least one function button 206, and a power button or switch 207. The multifunction device 104 may display a plurality of application icons on the touch screen 202. One of these icons may be the vital signs scanning application software icon 140.

Figure 2B:
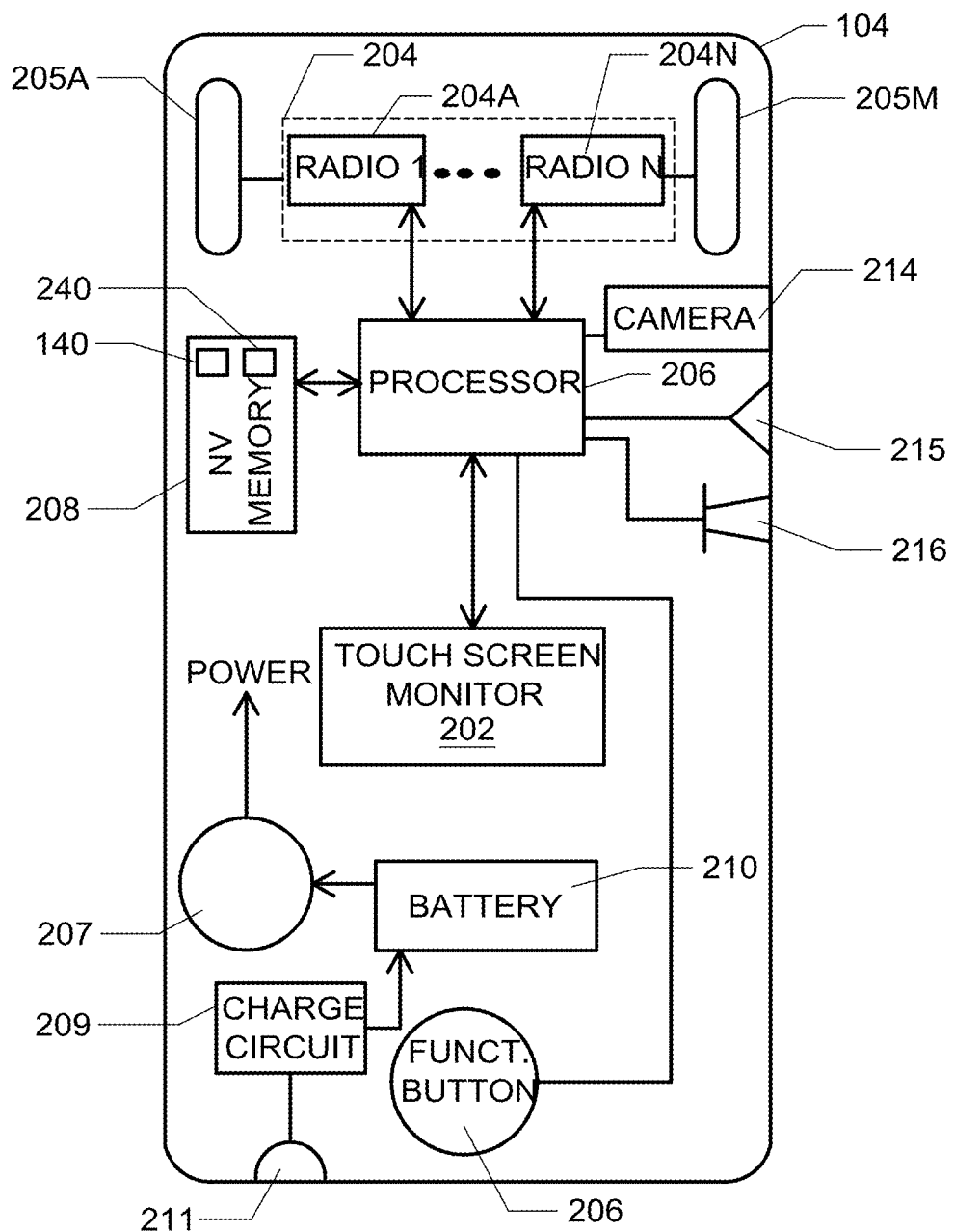
FIG. 2B illustrates a schematic representation of the components of the portable wireless multifunctional device.

Referring now to FIG. 2B, a block diagram of the personal wireless digital device 104 is illustrated. The portable wireless multifunction device 104 may be a smart phone, a tablet computer, a portable music player, or a wireless portable storage device, for example, that include a processor, a touch screen, and a memory from which application software instructions may be executed.

As shown in FIG. 2B, the portable wireless multifunction device 104 includes a touch screen monitor 202, one or more wireless radio transmitters-receivers (wireless radios) 204A-204M coupled to their respective antenna 205A-205M, a processor 206, non-volatile memory 208, at least one function button 206, and a cover button 207 that can switch power on to each electronic circuit within the portable wireless multifunction device 104. At least one of the wireless radios 204A-204M are compatible with the wireless radio in the wireless vital signs scanner 102.

The portable wireless multifunction device 104 may further include a camera 214, a microphone 215, and a speaker 216 coupled to the processor 206 as shown. Furthermore the portable wireless digital device includes a battery 210 coupled to the power button 207. Typically the battery 210 is a rechargeable battery such that an external power source may be coupled thereto via an external power connector 211 and a charge circuit 209.

Non-volatile memory 208 of the personal wireless digital device may store the vital signs scanning application software 140 and data 220 related to the vital signs scan application software. The processor 206 can read and write to the non-volatile memory such that the vital signs scanning application software can provide a user interface to a user via the touch screen display device 202. As discussed previously, the initial vital sign scanning window 140I may be provided as shown in FIG. 1C.

The camera 214 of the portable wireless digital device 104 may take photographs of a user's conditions or symptoms via the photograph entry button 175 of the user interface. The photographs may be stored as part of the data 240 in the non-volatile memory. The microphone 215 in the portable wireless multifunction device 104 may optionally be used to capture body sounds similar to the microphones in the scanner 102, as is shown in FIGS. 1E-1F.

The speaker 216 of the portable wireless digital device 104 may optionally be used to provide audible user feedback to the user of the vital signs scanner 102 to improve the vital signs scan quality as is discussed herein.

Referring now to FIG. 3A, an exemplary scanning window 140A is shown being displayed by the touch screen display device 202 of the portable wireless multi-function device 104. The scanning application software 140 generates the various images consisting of a scanning progress bar 310, a scanning icon 312, a first vital signs graph 314A, a second vital signs graph 314B, one or more result buttons 320, and one or more status icons 324.

The status icon 324 may be a wireless connection status icon indicating that the portable wireless digital device 104 is connected to the vital signs scanner 102. The button 320 may be a results button to which to switch to another scanning window/screen of a user interface provided by the scanning application software 140. The scanning icon 312 may include the plurality of color bars 312A-312E that randomly vary in color and length to indicate that scanning is occurring. The scanning progress bar 310 illustrates the progress of the scanning session being performed by the portable wireless vital signs scanner 102. In this case data is being sent from the scanner 102 to the portable wireless multifunction device 104.

Briefly referring back to FIG. 1C, the initial window 140I includes a user menu button 162 that may be used to display a users menu on how to operate the vital signs scanner. The initial window 140I may further include a graph button 165 to plot prior scan data stored in the device 104 and display it as graphs in a window.

In FIG. 3A, the first vital signs graph 314A may be an electrocardiogram (ECG) graph to illustrate the electrical activity of the user's heart where heart rate and other diagnostic features can be obtained. This waveform is captured by the scanning process of the portable wireless vital signs scanner 102. The second vital signs graph 314B may be a photoelectric plethysmogram (PPG) display from the data obtained by the pulse oximeter that captures a user's blood volume pulse of both oxygenated and deoxygenated blood. From the photoplesmography waveforms (oxygenated and deoxygenated) a user's oxygen saturation can be obtained.

Referring now to FIGS. 3B-3C, a scanning results window/screen 140B is shown being displayed by the touch screen display device 202. The exemplary scanning results window 140B may be generated by the user after selecting the results button 320 shown in FIG. 3A. The scanning results window 140B includes a plurality of vital signs icons 333A-333E, a plurality of associated measurements 332A-332E, and a plurality of associated vital sign text 331A-331E. The vital signs 331A-331E indicated may be heart rate, breathing rate, temperature, blood pressure, and oxygenation. The associated vital signs icons 33A-33E may be a heart icon, a breathing icon, a thermometer icon, a blood pressure icon and an oxygenation icon respectively.

The actual measurements captured during the scanning process are illustrated by the numeric number values 332A-332E. For example, the heart rate of 109 is shown near the heart icon 333A and the heart rate text 331A. Numeric values 332A-332E may be the average measurements captured during the scan that was immediately performed recently. The measurements 332A-332E are illustrated near their respective icons 333A-333E and the respective text indicating the vital sign that was measured. The results of the scan are typically automatically saved. However, a function button may be required to delete those scan results from the wireless portable multi-function device 104 or alternately a button to upload those results to a storage server.

FIG. 3D is an illustration of an exemplary window of the vital signs scanning application on the portable wireless device. In this exemplary window displayed on touch screen 202 of the multifunction device 104, the vital signs scanning application 140 is prompting the user to select a second scan. A second scan may be selected by touching scan virtual button 342 or using a finger gesture on the touch screen. A third scan may also be selected after the second by touching scan virtual button 342 or using a finger gesture on the touch screen. The third scan may be performed at the chest region to measure respiration rate and collect body sounds. The user may desire to skip a secondary scan by touching a skip scan virtual button 344.

Figure 4A:
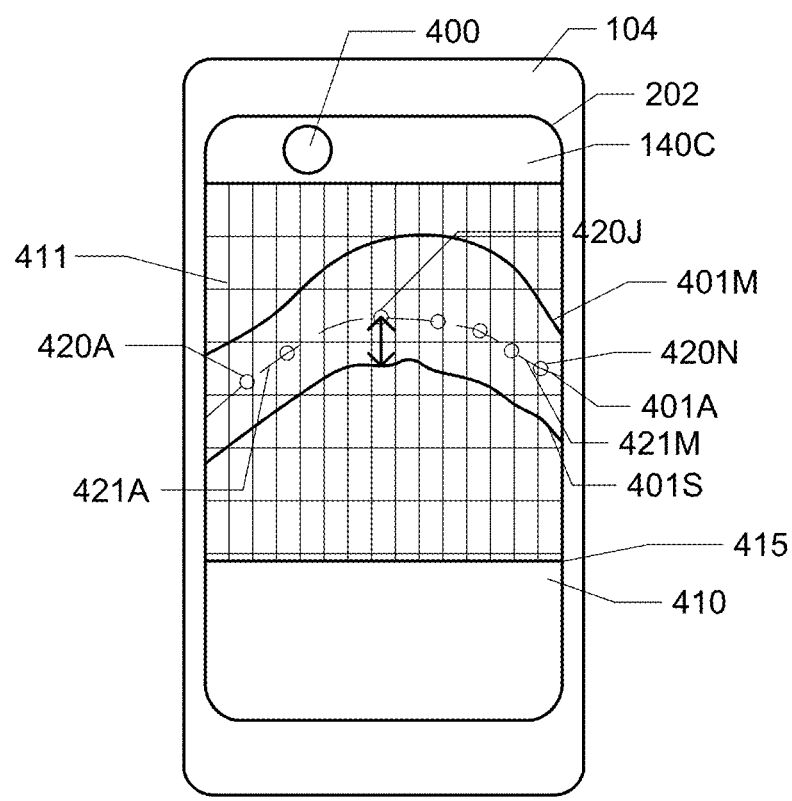
FIGS. 4A-4B illustrate a temperature averaging window generated in a touch screen of the portable wireless multifunction device by the vital signs scanning software application.
Figure 4B:
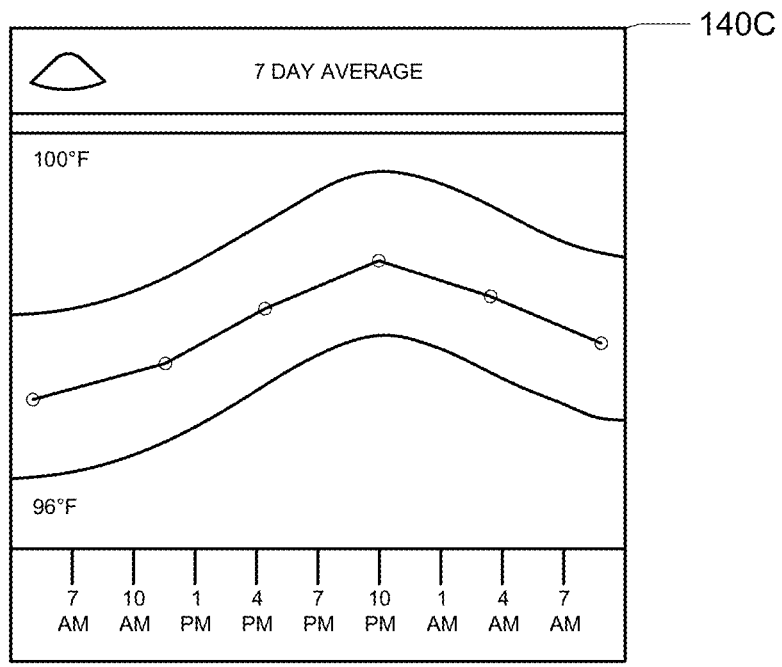

Referring now to FIGS. 4A-4B, a temperature averaging window 140C is shown being illustrated in the touch screen 202 by the scanning application software 140. This may be displayed as a result of selecting the graph button 165 of the initial scanning window 140I. The temperature averaging window 140C could include a textual heading 400 illustrating the types of graph that are plotted below. The textual heading 400 may recite "seven-day average" to let a user know that one or more seven-day average graphs are being displayed below. The portable vital signs scanner 102 may be used periodically throughout a 24-hour period each day. The seven day average may look back over a seven day window and time, plotting an average curve 401A, a maximum curve 401M, and a minimum curve 401S. The vital sign measurements are plotted on the Y-axis 411 and a time as the time of day on the X-axis 410. The portable wireless vital signs scanner 102 is expected to be used daily at multiple times during a day. In this, manner the vital signs of the user are captured periodically during the day by the vital signs scanner 102 and the personal portable wireless device 104 of the scanning system 100. The maximum curve 401M and the minimum curve 401S may be illustrating plots of the maximum value and minimum values over all scans that were previously performed. The time of day axis 410 illustrates periodic time values during the span of a 24-hour day. In one embodiment, the far most right point of the curves represents the given time of day 415 of a sliding window. In another embodiment, the time axis is fixed and the curve 401A grows from left to right during the time period as scans are made and time actually progresses. The scan points 420A-420N are illustrated along the average curve 401A. The scan points 420A-420N may represent actual scans during the day or some measure of average during the preceding seven-day period. Interpolation lines 421A-421M may be inserted between each scan point to show a trend line of how the vital sign that is measured varies during times of the day. For example, scanning point 420J may represent a scan that took place between 4:00 and 7:00 pm and how the body trends towards that during that time of day.

The illustrated seven day average graph illustrated in FIGS. 4A-4B shows a body temperature graph. This is for illustration purposes only. The vital sign measurement curves could be temperature curves, blood pressure curves, oxygenation curves, heart rate curves, breathing/respiration rate curves, for example, that represent measurements that are scanned by the vital signs scanner 102.

As more information is captured by the scanner 102 and stored in the personal portable multi-function device 104, additional results may be plotted over time to generate the curves for display by an averaging window, such as vital signs window 140C.

Figure 5A:
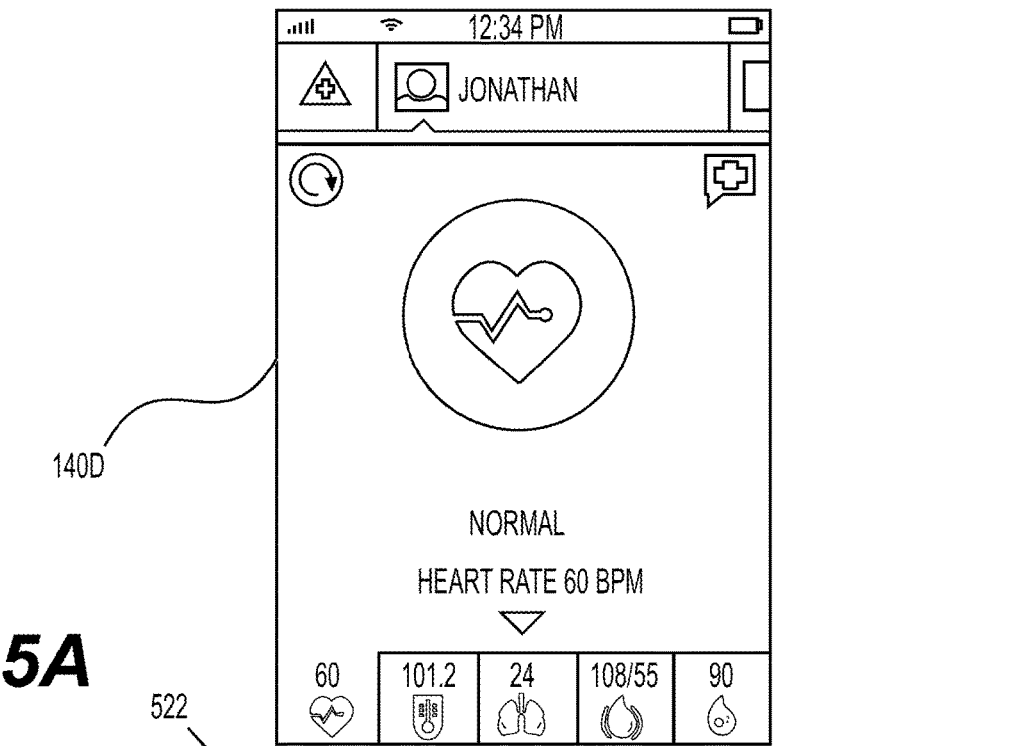
FIGS. 5A-5E illustrate prognosis windows for vital signs in a touch screen of the portable wireless multifunction device.
Figure 5B:
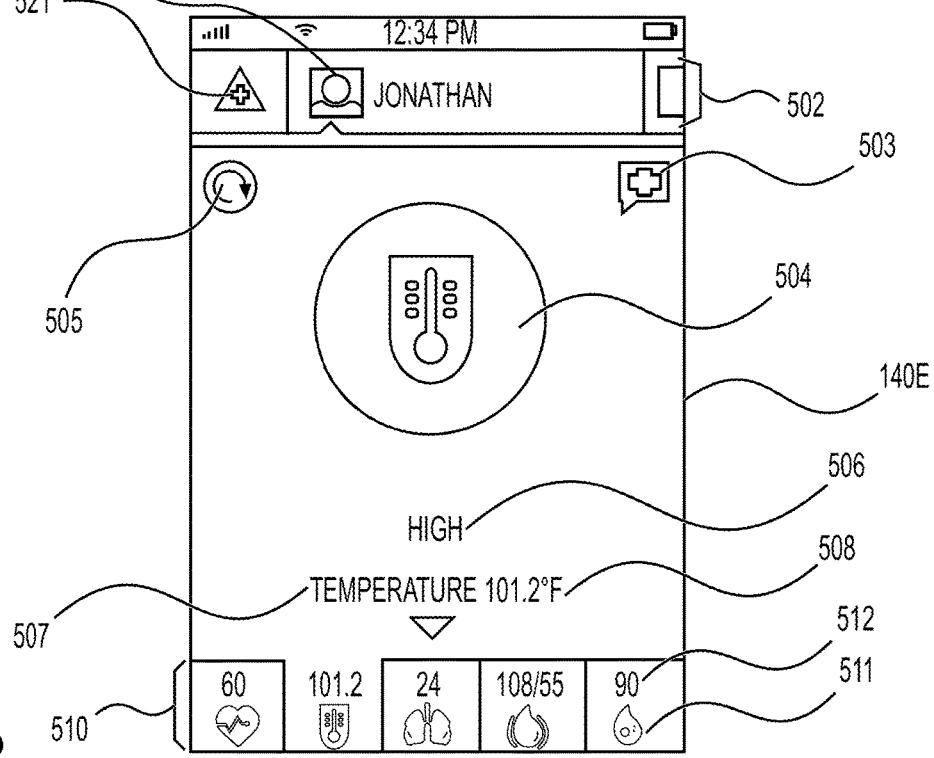
Figure 5C:
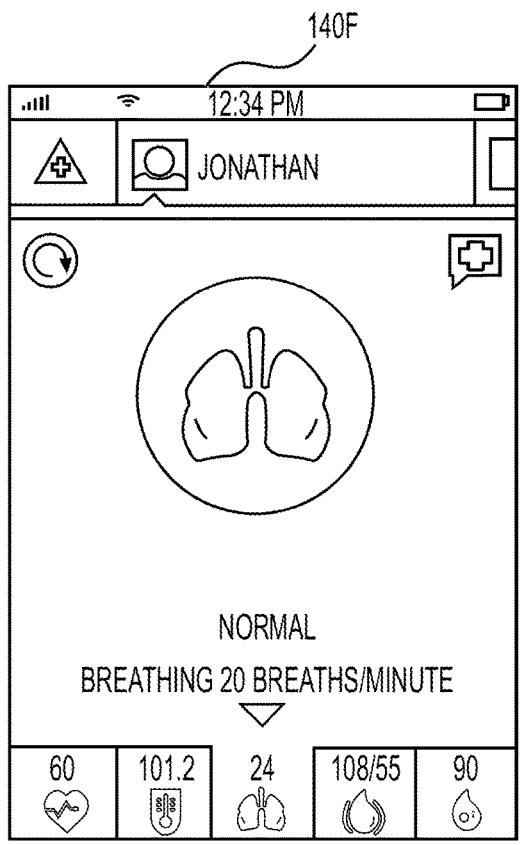
Figure 5D:
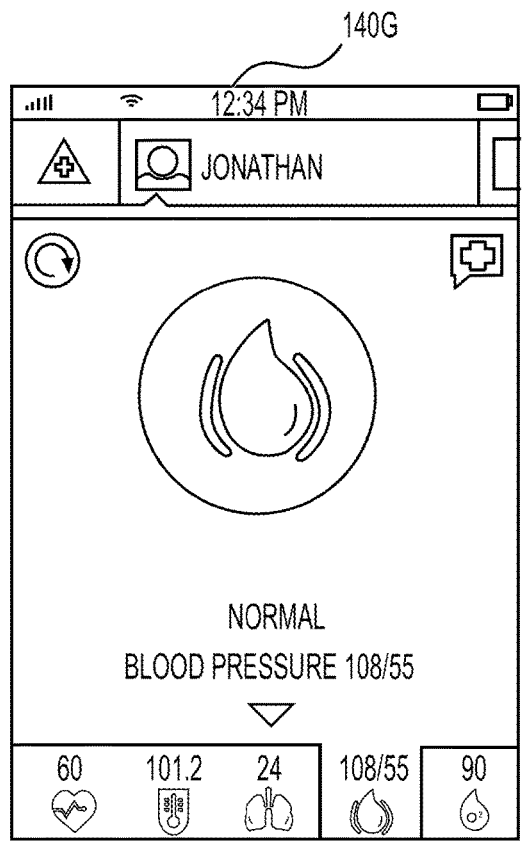
Figure 5E:
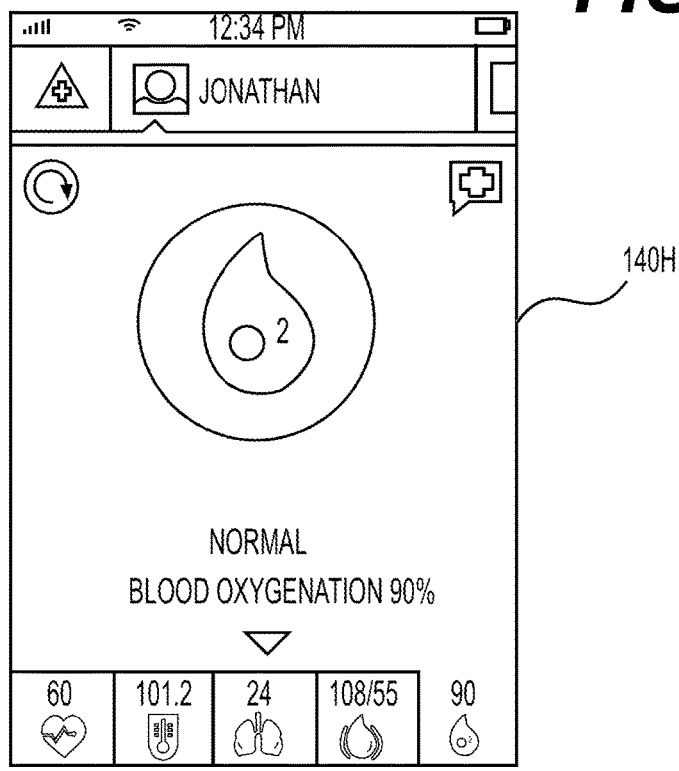

Referring now to FIG. 5A-5E, a plurality of prognosis windows 140D-140H are illustrated. In FIG. 5A, the heart rate prognosis window is shown. In FIG. 5B, the temperature prognosis window 140E is illustrated. In FIG. 5C, a breathing rate prognosis window 140F is illustrated. In FIG. 5D, a blood pressure prognosis window 140G is illustrated. In FIG. 5E, a blood oxygenation window 140H is illustrated. These windows may be selected through the use of the vital signs icons 333A-333E acting as buttons to display the respective prognosis window.

As illustrated in FIG. 5B, each prognosis screen 140D-140H, may include a navigation bar 502, one or more function buttons 503, a vital signs icon 504, a return button 505, a conditions indictor 506, a vital signs indicator 507, a measurements value indication 508, and a vital signs bar 510. The navigation bar 502 may allow a user to navigate the various screens of the vital signs application scanning software 140. For example, a scan screen icon/button 521 may be provided to jump to the scanning screen. A prognosis screen icon/button 522 may be provided to jump to the prognosis screens 140D-140H.

The vital signs bar 510 may be provided to navigate through the various vital signs prognosis windows/screens 140D-140H as well as providing a snapshot of the values of each of the vital sign measurements. In that case the vital signs bar 510 includes a measurement value indicator 512 and a vital signs icon 511 for each of the vital signs that are scanned and captured by the vital signs scanning system 100.

The return button 505 may be used to return to the previous screen that was displayed by the user interface of the scanning application software 140. The function button 503 may be an add a note button to add text about a user's condition or circumstances under which a scan was taken. The vital signs icon 504 indicates at a glance what prognosis window is being displayed.

The conditions indictor 506 for each prognosis screen will provide an indication of the most recent scan in comparison with an expected average value for a given user. For example, a temperature's vital sign is illustrated in FIG. 5B as having the condition indication of high due to a measured value of 101° F.

In the vital signs bar 510 the measurement indicator 512 and the vital signs icon 511 may be highlighted to indicate which prognosis screen is being illustrated at a glance.

Figure 6A:
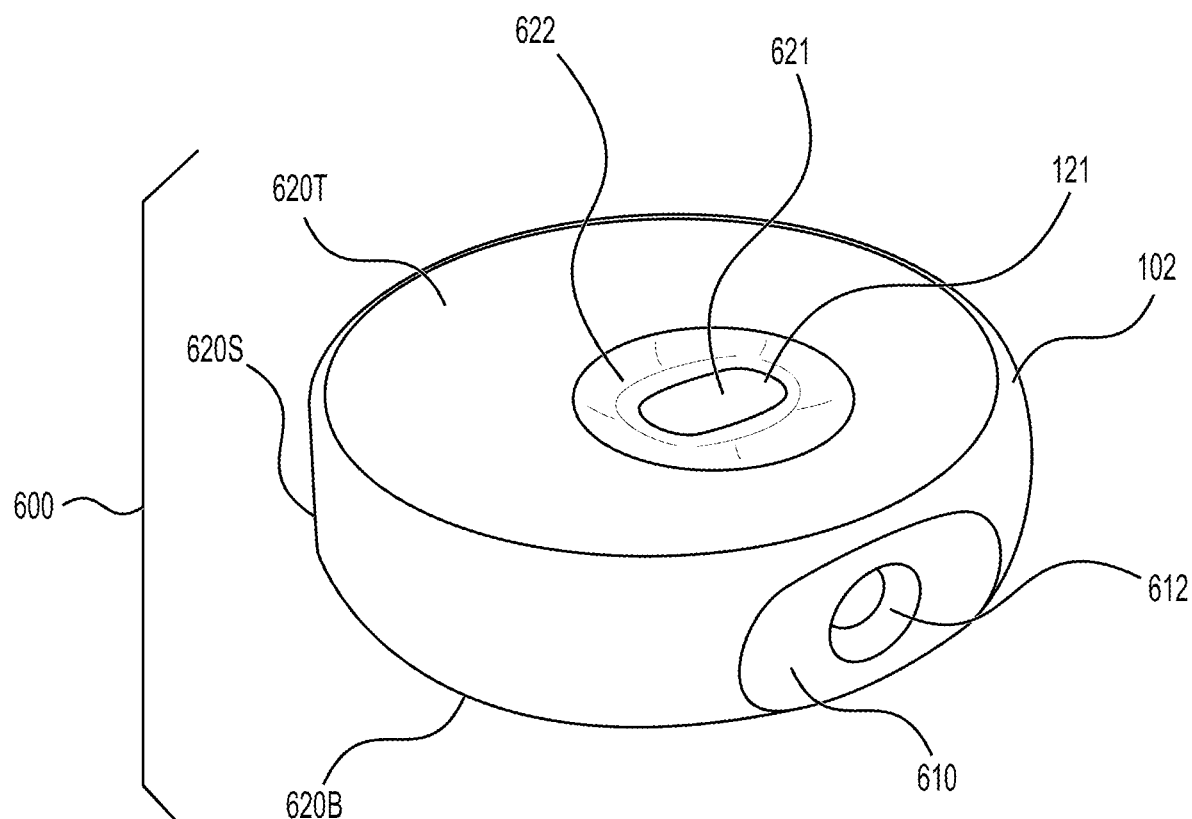
FIGS. 6A-6B are perspective views of an embodiment of the invention.

Referring now to FIG. 6A-6D, respective use of the portable wireless vital signs scanner 102 are illustrated. In FIG. 6A, a top front perspective view, the wireless vital signs scanner 102 includes a front electrode 610, and a front sensor 612 on a front side. The front electrode 610 is pressed against the user's forehead/temple, preferably at the temple, in order for the scanner 102 to make an electrical connection to the body of the user.

In one embodiment the scanner 102, a top sensor window 621 and a top electrode 622 are provided in the topside of the scanner 102. A top sensor 121 may be located underneath the top sensor window 621 to obtain a vital signs measurement from a user's finger that may be pressed on top of the window 621. A top electrode 622 may be used to form an electrical connection to a user's finger and complete a circuit of the user's body such as illustrated in FIG. 1A.

The housing 600 of the vital signs scanner 102 may generally be circular shaped and include a circular top housing 620G, a circular bottom housing 620B, and a hollow cylindrical surface 620S. The side cylindrical ring 620S may be concave, or convex over a portion of the surface. Alternatively, the cylinder side surface 620S may be a toroid shape over a portion of its body.

Figure 6B:
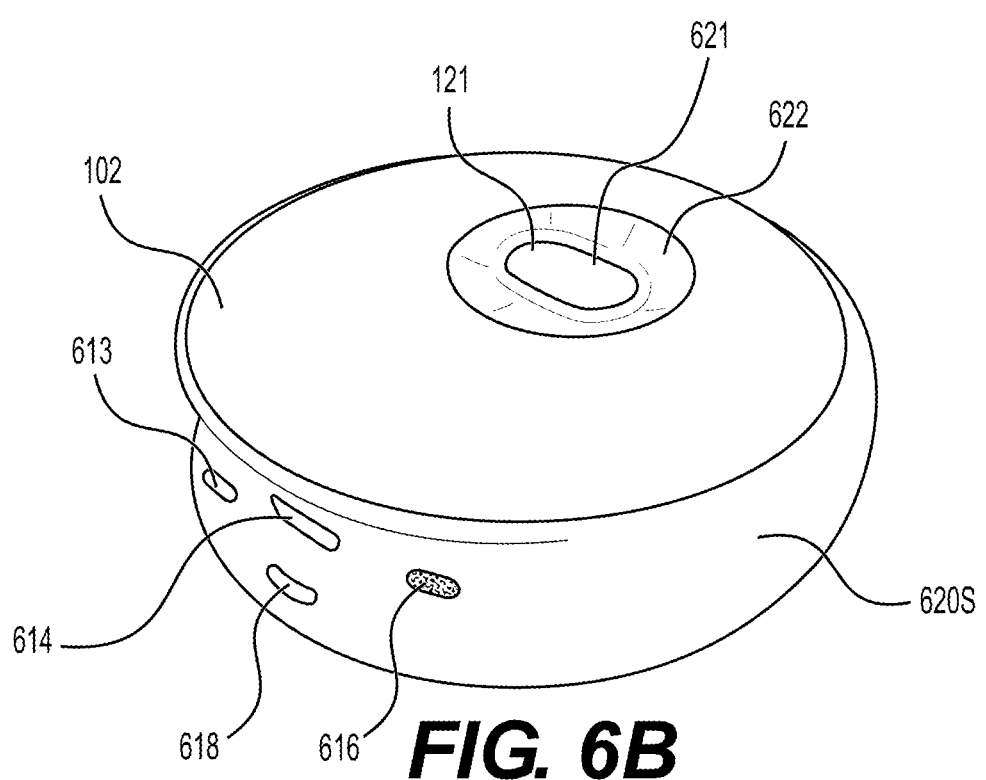

In FIG. 6B, a top back perspective view of the wireless vital signs scanner 102 is illustrated. The wireless vital signs scanner 102 illustrate various aspects of the invention in the side cylindrical surface 620S. The wireless vital signs scanner 102 includes a power button 613, a serial port connector 614, an optional wireless connection LED 618, and a power light-emitting diode 616. The power button 613 may be pressed to power the wireless vital signs scanner 102 on. The serial port connector 614 may be a micro universal serial bus connector to allow a micro USB cable to plug thereto. The micro USB port may provide an external power source to charge the rechargeable battery within the wireless vital signs scanner 102 and also may serve as a wired data port for updating firmware or transferring data to a computer or storage device. The optional wireless connection light-emitting diode 618 provides a visual indicator that the wireless vital signs scanner 102 is coupled to the wireless personal portable multi-function device 104 over its wireless communications channel 103A as illustrated in FIG. 1A. The power light-emitting diode 616 provides an indicator that the wireless vital signs scanner is powered on by the power button 613.

Figure 6C:
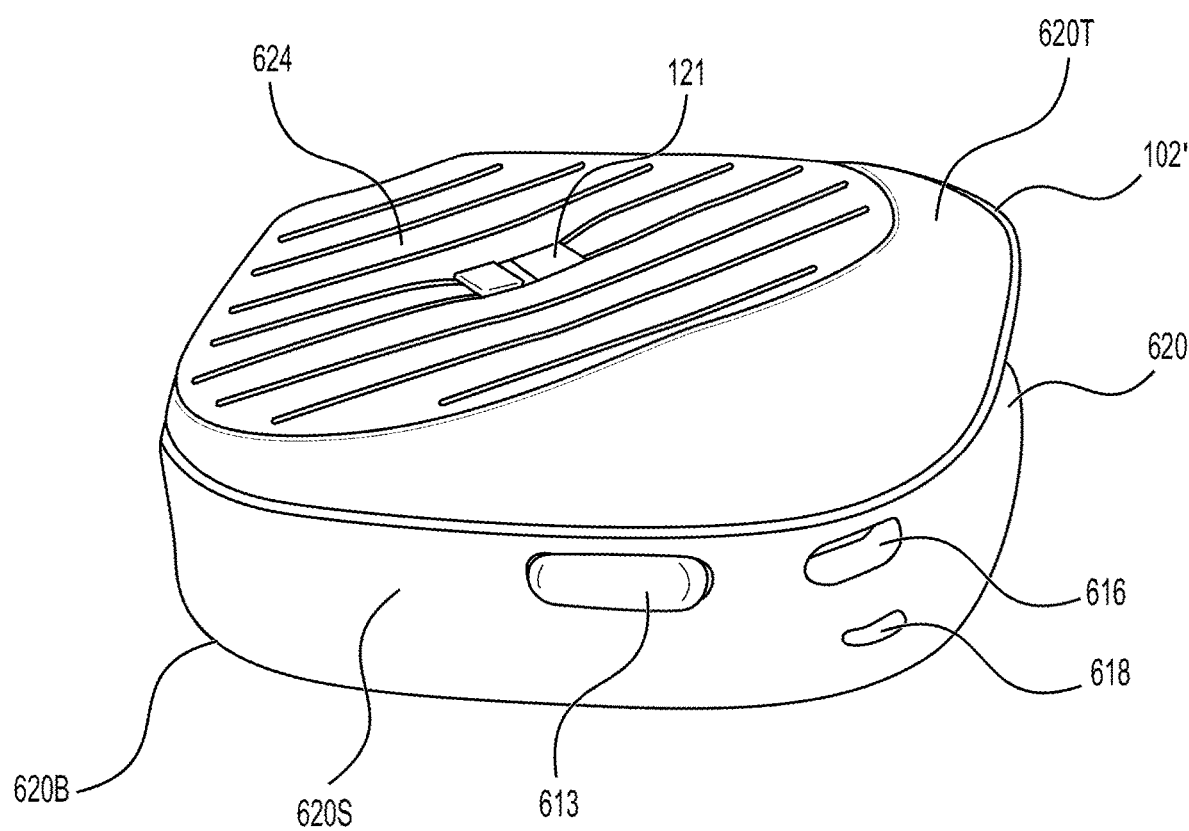
FIGS. 6C-6D are perspective views of another embodiment of the invention.

In FIG. 6C, a vital signs wireless scanner 102' is illustrated having a generally diamond shaped body housing 620. In this case the housing top 620T and the housing bottom 620B generally have a diamond or a square shape to match that of the side cylindrical surface 620S. The top or bottom housing portion 620T may each include a gripping surface 624 with corrugations or channels so that a user may comfortably and securely hold the wireless vital signs scanner 102'. The gripping surface 624 may be formed of a conductive material to aid the top and or bottom electrodes in forming an electrical connection to a user's body.

Figure 6D:
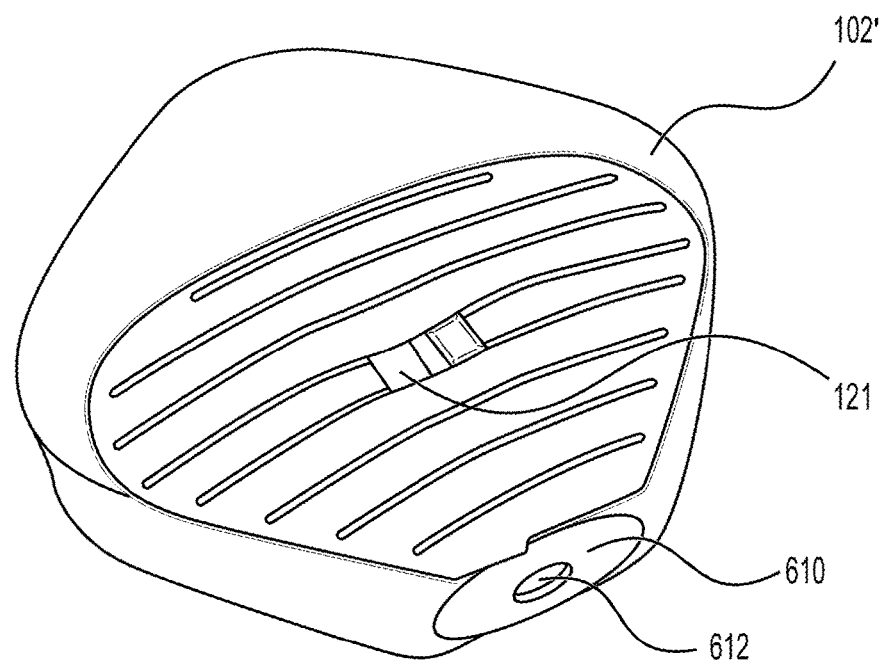

Referring now to FIG. 6D, a top front perspective view of the wireless vital signs scanner 102' is illustrated. The wireless vital signs scanner 102' includes the front electrode 610 and front sensor 612.

While the electrode 622 and the gripping surface 624 are illustrated in the top housing 620T, they may also be implemented in the bottom housing portion 620B instead of the top. Instead of an index finger making a connection with a top electrode 622, a thumb finger may couple to a bottom electrode (not shown) to provide a larger surface area contact to the body in the bottom housing portion 620B.

Figure 7A:
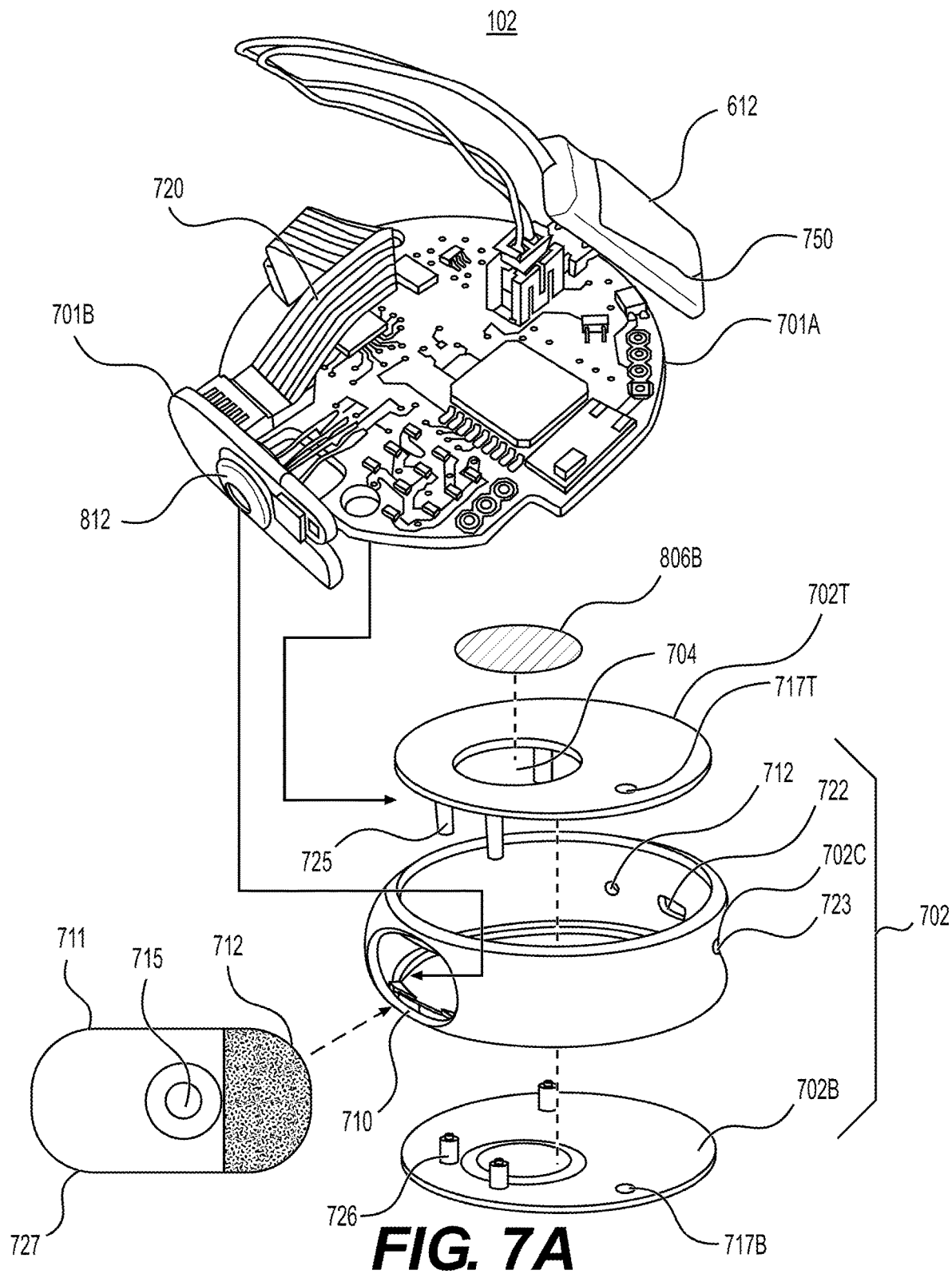
FIG. 7A is an exploded view of the exemplary portable wireless vital signs scanner.

Referring now to FIG. 7A, an exploded view of the wireless vital signs scanner 102 is illustrated. The exterior components of the wireless vital signs scanner 102 are formed of parts that can be wiped clean by a damp towelette or a disinfecting wipe. In this manner, the scanner 102 may be shared by users in a family with less worry about spreading bacteria and germs. Each user may have a personal profile or preferences stored in the scanning software application 140.

The wireless vital signs scanner 102 includes a main printed circuit board 701A and a daughter printed circuit board 701B coupled perpendicular to the main circuit board 701A. Because the scanner 102 is wireless, it includes a rechargeable battery and a connector port to which a cable may connect to recharge the battery. Preferably the battery may be charged in an hour or less. If the scanner 102 is used a few times a day, the charge of the rechargeable battery may last about a week. The main print circuit board 701A, the daughter printed circuit board 701B, and the rechargeable battery form an electronic sub-assembly 701.

The electronic sub-assembly 701 is inserted into a housing 702 of the vital signs scanner 102. The sensors on the front daughter board 701B are aligned into a front sensor opening 710 in the side housing ring 702C of the housing 702. A ribbon cable 720 electrically connects the front daughter board 701B to the main print circuit board 701A. A sensor 812 in the front daughter board 701B includes electrical leads that are coupled to the main printed circuit board 701A.

The main printed circuit board 701A is inserted into the housing ring 702C so that a serial bus connector 612 aligns with the connector opening 722 and the front sensor 812 is aligned into the front sensor opening 710. A top/bottom electrode 806B covers over an opening 704 and is electrically coupled to the main printed circuit board 701A and an ECG circuit mounted thereto.

The housing 702 of the wireless vital signs scanner 102 includes a top housing portion 702T with a top electrode 806B, a side housing ring 702C, and a base housing portion 702B. The orientation of the housing 702 for the scanner 102 may be altered such that the housing base 702B becomes the housing top 702T and the housing top 702T becomes the housing base 702B with a bottom electrode 806B to couple to a thumb. Electrodes may also be in both the housing base 702B and the housing top 702T to provide a lower resistive coupling to the user's body.

The top housing portion 702T includes a microphone opening 717T and a plurality of posts 725 and an electrical sensor opening 704. The housing base 702B may include a microphone opening 717B and a plurality of pillars 726 that can interface to the posts 725 when the housing is assembled together about the printed circuit boards.

The wireless vital signs scanner further includes a front cover 711 to fill in the front sensor opening 710 in the side housing ring 702C. The front side cover 711 includes a plastic cover portion 712 and a front electrode portion 727 with a lens 715 transparent to thermal wavelengths to allow the sensor 812 beneath it to capture a measure of temperature. The plastic cover 712 is also transparent to various wavelengths of light that are used by the vital signs sensors. The front electrode portion 727 of the front cover 711 is formed of a conductive material, such as stainless steel metal, to form a circuit when pressed up against the user's body at the forehead/temple, finger, chest or elsewhere. The shape of the front electrode 727 can vary with the shape of the wireless vital signs scanner 102.

The side housing ring 702C includes one or more LED openings 712 to receive the power light-emitting diode 616 and the optional wireless connection light-emitting diode 618. The side housing ring 702C further includes a power button opening 723 through which the power button 613 may extend.

Figure 7B:
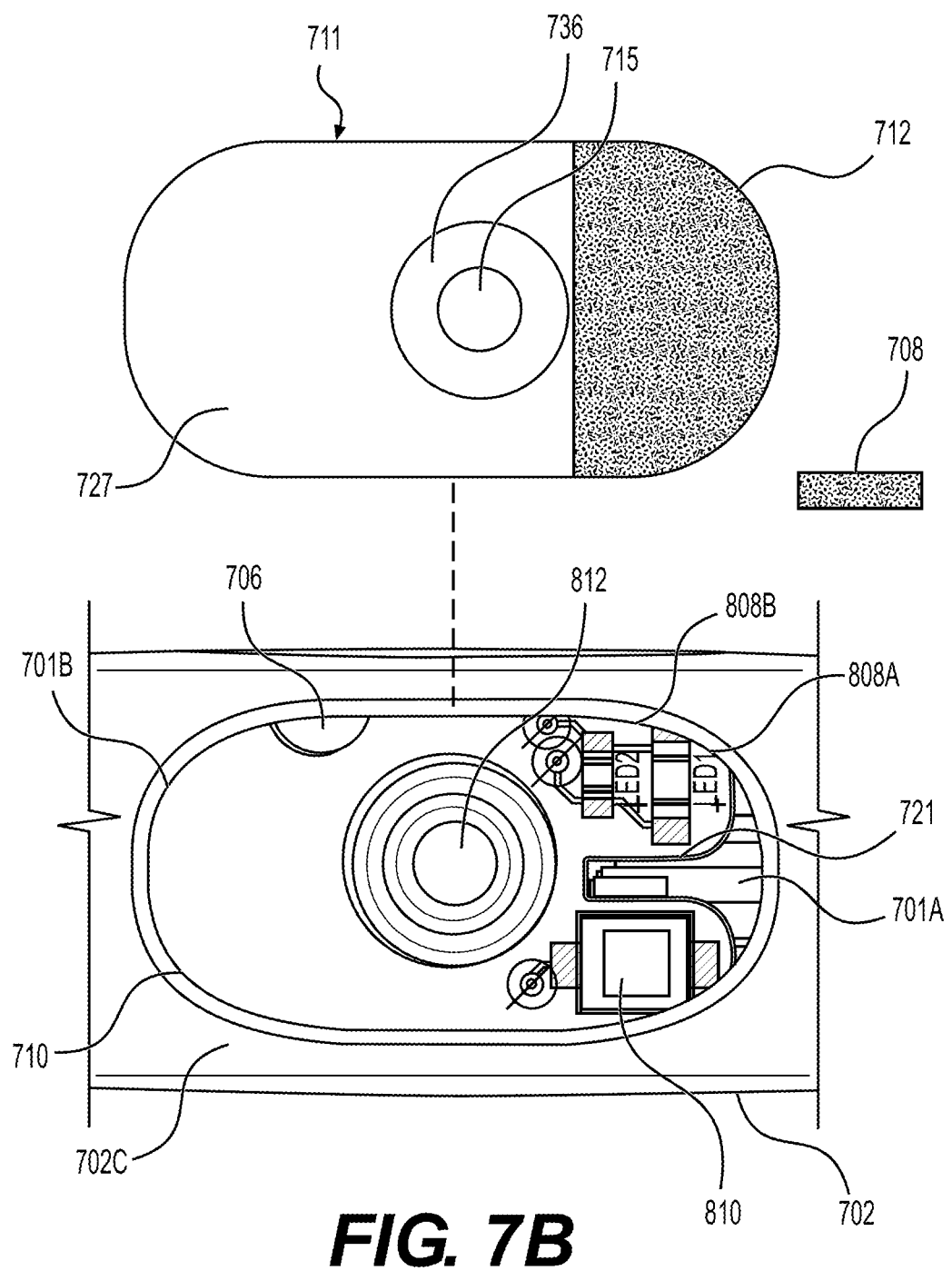
FIG. 7B illustrates a partially assembled exemplary portable wireless vital signs scanner

FIG. 7B illustrates a partially assembled wireless vital signs scanner 102. Through the front opening 710 in the side housing ring 702C, the front daughter printed circuit board 701B includes a slot opening 721. The slot opening 721 may be used to receive a shade 708 that separates the LEDs 808A-808B from the photo diode 810. The shade 708 deters light emitted by the LEDs 808A-808B from directly being impinged onto the photo diode 810. The wire (not shown in FIG. 7B) from the front electrode 727 may inserted through the opening 706 and then coupled to the main PCB and the ECG circuit. The front cover 711 can then assembled to cover over the front opening in the side housing ring 702C of the housing.

The daughter printed circuit board 701B is arranged to be substantially perpendicular with the main printed circuit board 701A. As previously discussed, the front cover 711 includes a transparent cover portion 712 and a metallic conductor portion 727, and the lens 715. The transparent cover portion 712 covers over one or more light-emitting diodes 808A-808B generating various wavelengths of light, and a photo diode 810 that receives various wavelengths of light. The light generated by the light-emitting diodes 808A-808B is shined onto the user's forehead and reflected back to the photo diode 810. Light with known time periods may be generated by the light emitting diodes (LEDs) 808A-808B with different wavelengths and radiated onto a user's forehead/temple. The reflection is detected by the photo diode 810 to form an electrical signal that is analyzed. In this analysis of the signal generated by the reflected lights of different wavelengths, a measure of oxygenation in the blood stream may be generated.

The front side cover 711 includes the transparent lens 715 with a center aligned into the optical axis of the front side sensor 812 so that additional vital signs measurement may be made from the forehead/temple of the user. An opening 706 in the daughter board 701B allows a wire to pass through from the front electrode 727 and be coupled to a wire trace on the main PCB that is coupled to the ECG circuitry mounted thereto. When pressed against the user, the metallic electrode portion 727 of the front side cover 711 makes an electrical contact to the forehead/temple or other body portion of the user. An insulating ring 736 under the electrode portion 727 of the front side cover may be used to isolate any metal of the infrared thermometer 812 from the electrode portion 727.

FIG. 8A illustrates a functional block diagram of electronic circuitry 800 within the portable wireless vital signs scanner 102. The personal portable wireless vital signs scanner 102 associated with a given user profile stored in the user data of the wireless personal multifunction device 104. The wireless communication channel 103A between the scanner 102 and the multifunction device 104 may be a secure connection with information passed between each. The devices are typically paired to each other by a code so that no other wireless device may utilize the wireless communication channel 103A. A different wireless communication channel 103B may be generated between the vital signs scanner 102 and a personal computer 150, for example. Each of the wireless communication channels 103A, 103B may be a Bluetooth communication channel, for example, in which case the signal strength between each over a Bluetooth communication channel is relatively short with a limited distance over a range between zero and twenty-five feet, for example.

Referring now to FIG. 8A, electronic circuitry 800 of the portable wireless vital signs scanner 102 includes a processor 840 at the heart of the system. The processor 840 may be a reduced instruction set processor operating with embedded operating system software. In one embodiment of the invention, the processor is an ARM processor operating with MICRIUM's embedded real time operating system (RTOS).

To provide the wireless communication channels 103A, 103B, a wireless radio 870 is coupled to the processor 841. The wireless radio 870 is coupled to an antenna 871 that could be internal, as part of an overall radio system, or external to the wireless radio 870. An optional light emitting diode 848, used as a wireless connection indicator, is coupled to the wireless radio to indicate a successful pairing with the personal portable wireless digital multifunction device 104. To scan for vital signs over a period of time such as 10 seconds, the electronic system 800 includes an infrared thermometer 812, an accelerometer 885, a pulse oximetry sensor and a pulse oximetry circuit 880, and analog electrocardiogram circuitry 860. Coupled to the electrocardiogram circuitry 860 is the bottom or top electrode 806B, the front electrode 711, bottom/top electrode connection, and the front electrode connection 806F. As shown in FIG. 1A, a portion of a human body is coupled to the front electrode 711 and the top/bottom electrode 806B to form a circuit.

The pulse oximetry circuit 880 is coupled to a pair of light emitting diodes 808A-808B. Each of these emit light patterns that are reflected off of the user's forehead/temple internally. The reflected light is captured by a photodiode 810 and coupled to the circuit 880. That is, incident light 891 from the light emitting diodes 808A-808B reflects internally off the user's head 116 as reflective light 892 which is received by the photodiode (PD) 810.

The infrared thermometer 812 detects the surface temperature of a use's forehead/temple (or elsewhere) by measuring thermal radiation (referred to as Blackbody radiation) 813 emanating from the head 116 (or other body portion to which the scanner is pressed) of a user.

To power the circuits in the system 800 of the personal portable wireless vital signs scanner 102, a rechargeable battery 850 and a voltage regulator and battery charge controller 854 are coupled together into the circuits in the system 800 when the switch 852 is closed. The battery charge controller 854 is coupled to power pins of a serial connector 856 to receive an external DC voltage supply. The external voltage supply may be used to recharge the battery and power the system 800 when it is connected. The rechargeable battery 850 may hold a charge for a period of seven days, even while scanning multiple times during each day, due to the low power consumption of the circuitry and the limited period of time needed to perform a scan of the vital signs of a user. That is, the vital signs scanner 102 is not expected to be continuously powered on during a day, but powered up periodically to perform the scans as needed.

The processor 840 may include a processor memory 841 to store system instructions to control the circuitry in the system to obtain the scans and process the information obtained through those scans into a proper user format. To store the user data from each of these scans, a nonvolatile memory 844 is coupled to the processor 840. The nonvolatile memory 844 may be soldered to a printed circuit board with the processor 840. In an alternate embodiment of the invention, a connector 845 is provided so that the nonvolatile memory 844 is a removable memory card so that a user's data may be transferred from one scanner to the next, if needed.

A power LED 851 may be coupled to the processor 840 to provide an indication that the electronic system 800 is powered up. The system can be manually shut down via the scanning software application 140 so that the scanner 102 powers off. However, the scanner 102 can also automatically shut off after a predetermined period of time to conserve power and a charge on the rechargeable battery 850. The user then just needs to press the power switch 852, once again, to turn the system back on and scan for vital signs of a user.

The processor 840 includes one or more analog digital convertors 842 in order to receive analog signals from the infrared thermometer 812, accelerometer 885, pulse oximetry circuits 880, and ECG analog circuits 860. Electronic system 800 may further include a stereo microphone 875 consisting of a top microphone 875T and a bottom microphone 875B each coupled to a stereo microphone amplifier 874. The stereo microphone amplifier may have its own analog to digital converter, or the processor's analog digital convertor 842 may be used to convert analog signals into digital signals. For example, an ECG analog signal may be converted into digital signals with the analog digital convertor 842 of the processor. The stereo microphone 875 captures audio signals near the wireless vital signs scanner 102. The accelerometer 885 captures movement of the portable wireless vital signs scanner 102.

The combination of the audio information and the movement information may be utilized to determine the quality of the scanning information being obtained by the vital signs capturing circuitry. For example, the stereo microphone 875 may be used to capture noise from a user talking and plot that on a graph indicating noise spikes, or noise lines 330, such as shown in FIG. 3A. This provides feedback to a user about the quality of the scan at these intervals. The accelerometer 885 and the motion information may be similarly used to make a judgment about the quality of the vital signs scanned information being captured by the vital signs circuitry of the infrared thermometer 812, the pulse oximetry circuits 880, and the ECG analog circuits 860.

The microphones 875 in the portable wireless scanner 120 may also be used to capture body sounds such as shown in FIGS. 1E-1F and store the captured body sounds in memory 844 to improve vital sign measurements or as a potential symptom of a medical condition of the users body. For example, heart beat sounds 155 may be captured by the microphones 875 when the scanner 102 is positioned against skin of the chest 114 near ones heart 156, as is illustrated in FIG. 1E. As another example, lung or breathing sounds of air entering and exiting ones lungs, respiration sounds 157, may be captured by the microphones 875 when the scanner 102 is positioned against skin of the chest 114 near a lung 158 in ones body, as is illustrated in FIG. 1F.

To further optimize scanning results, scan quality algorithm monitor the vita signs scanning process and can provide feedback (visual and/or audible) to the user, such as through the multifunction device 104.

An optional audible sound generator 847 in the scanner 102 may be coupled to the processor 840 to provide audible user feedback to the user during the scanning process. The user feedback may help the user to perform better vital signs scan with the wireless vital signs scanner 102 and acquire a higher quality of vital signs measurements. The audible sound generator 847 may generate alert sounds indicating when the scanning process begins and ends. It may also generate an error signal indicating to the user that he is not properly using the scanner 102 and look for instructions on the device 104.

Figure 8B:
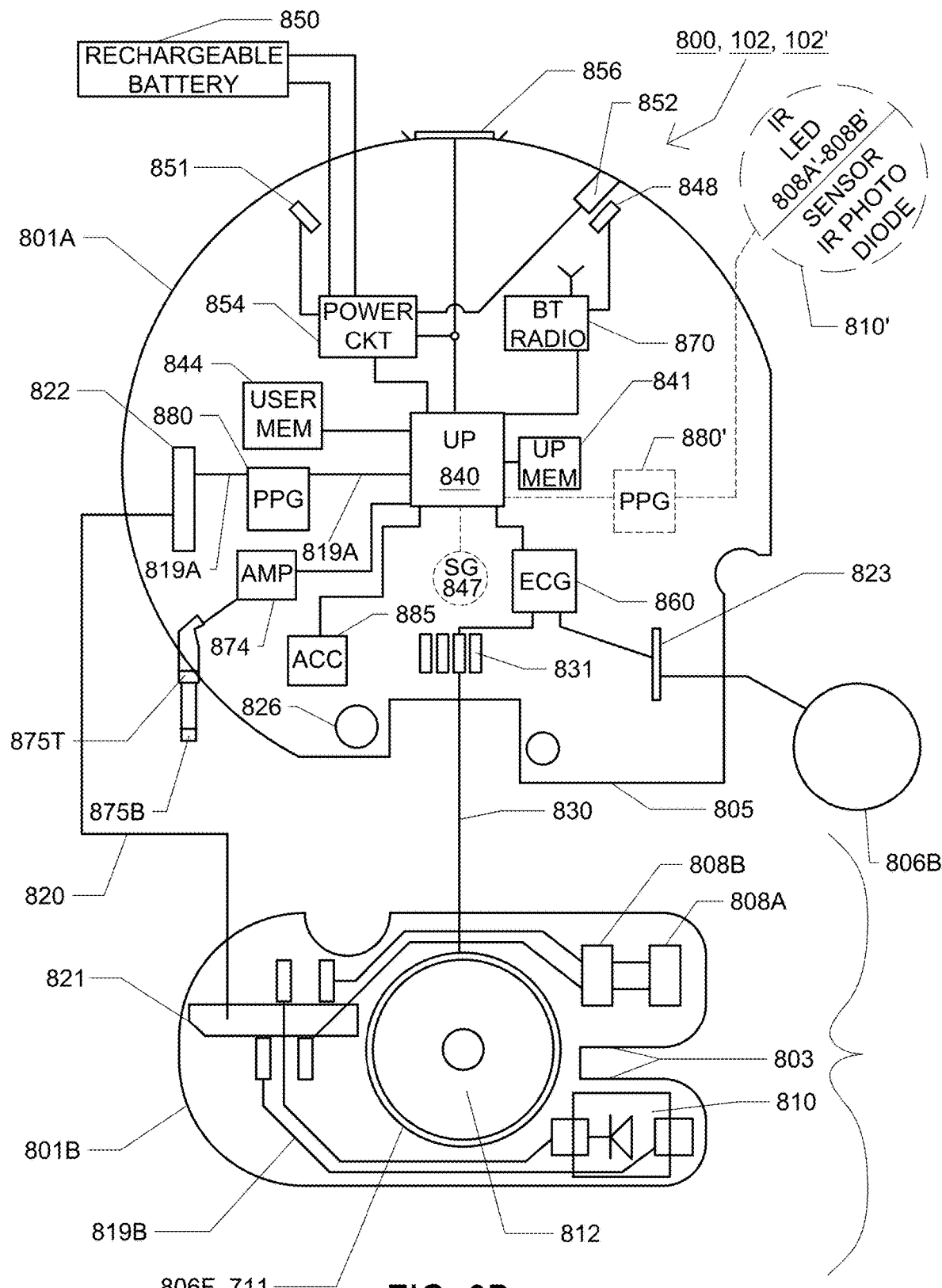
FIG. 8B illustrates a main printed circuit board coupled to a daughter printed circuit board with various electronic circuitry within the exemplary portable wireless vital signs scanner mounted to each.

Referring now to FIG. 8B, a sketch of the electronic circuits 800 is shown mounted onto the main printed circuit board 801A and the daughter printed circuit board 801B. FIG. 8B also illustrates alternate locations for electronic circuits in the system 800 for alternate embodiments of the vital sign scanners 102, 102'.

A slot 803 in the daughter printed circuit board 801B receives a shade device 708. Light emitted by the LEDs 808A-808B is shaded by the shade device 708 so that it may not directly impinge onto the photo diode 810 in the daughter PCB 801B. Reflected light, reflected off the user's body, is desirable to be captured by the photo diode 810.

Wire leads 830 of the IR sensor 812 and the front electrode contact 806F are coupled to pads 831 of the main printed circuit board 801A. First and second LEDs 808A-808B and the photodiode 810 are coupled to connector 821 by conductive traces 819B on the daughter printed circuit board 801B.

The main printed circuit board 801A has a plurality of wire traces 819A coupling circuits mounted thereto together. The daughter printed circuit board 801B includes a plurality of traces 819B coupling circuits mounted thereto to connector 821. A ribbon cable 820 is used to couple signals between the daughter memory card 801B and the main printed circuit board 801A for the oximetry circuit 880. The oximetry electronic circuit 880 is coupled between the connector 822 and the processor 840 on the main printed circuit board 801A. One set of one or more wire traces 819A couple the oximetry electronic circuit PPG 880 to the connector 822. Another set of one or more wire traces 819A couple the oximetry electronic circuit PPG 880 to the processor 840.

In accordance with one embodiment of the invention, if the oximetry sensors are moved to a top portion of the housing to sense oximetry through a finger, with the IRLEDs 801A'-801B' and the IR photodiode 810', the oximetry circuitry may be moved to the opposite side as the oximetry electronic circuit PPG 880' coupled between the processors 840 and the LEDs 808A'-808B', IR photodiode 810' and mounted in the top portion of the housing.

The bottom or top electrode 806B is formed of stainless steel to provide a good connection to either a thumb finger or an index finger. The electrode 806B is coupled to a connector 823 and to the ECG circuitry 860 on the main printed circuit board 801A.

The main printed circuit board 801A includes the processor 840, the wireless radio 870, the microprocessor memory 841 (either internal or external as shown mounted to the printed circuit board), an accelerometer 885, an amplifier 874, oximetry circuitry 880, 880', user memory 844, and battery charge circuit 854.

Top and bottom microphones 875T and 875B extend out from the main printed circuit board 801A by ribbon cables so that they may be mounted into the respective openings in the housing top and housing bottom. The microphones 875T, 875B may be coupled to the amplifier 874 which in turn may couple audio signals into the microprocessor 840. Mounted to the main printed circuit board is the power LED 851 and the connection LED 848. Further mounted to the main printed circuit board is a power on/off switch 852 coupled to the voltage regulator battery charge circuit 854 to signal for it to turn power on or off to components with the scanner 102. Additionally, mounted to the main printed circuit board 801A is a serial connector 856 coupled to the microprocessor. In one embodiment invention, the serial connector 856 is a micro universal serial bus connector.

An optional audible sound generator 847 may be mounted to the main PCB 801A and coupled to the processor 840 as shown. To avoid interference, the sound generator 847 may be positioned away from the microphones 875.

Main printed circuit board 801A includes a plurality of openings 826 that receive the pillars 725, 726 of the housing top 702T and housing base 702 B.

The daughter printed circuit board 801B includes a connector 821, light emitting diodes 801A-801B, and a photodiode 810 mounted thereto. The IR sensor 812 is inserted through a hole in the daughter PCB 801B, attached thereto with an adhesive, and supported thereby. The front electrode 806F around the IR sensor 812 is attached with an adhesive to the daughter PCB 801B for support.

The ribbon cable 820 couples signals of the light emitting diodes 801A-801B and the photodiode 810 regarding oximetry between the daughter board 801B and the main printed circuit board 801A for the oximetry circuit 880. With the terminals 830 of the IR sensor 812 coupled to the pads 831 of the main PCB 801A, signals of the IR sensor 812 regarding temperature are coupled into the processor 840. With the terminals 830 of the front electrode 806F coupled to one or more pads 831 of the main PCB 801A, signals of the ECG circuit 860 to measure heart activity (e.g., heart rhythm, heart rate, etc.) may be coupled into and out of a users body.

Thus, the personal portable wireless vital signs scanner integrates a plurality of sensors and a controller/processor together to synchronously obtain a plurality of vital signs at different times during a users day. Despite the integration of multiple sensors and a controller/processor into the scanner, the vital signs scanning device has a relatively low production cost. The integration with a ubiquitous consumer electronic device pre-owned by many users, the personal wireless multifunction device (e.g. smartphones, tablets, etc.), to display the vital signs data with vital signs scanning software, also keeps the costs low of the overall personal vital signs scanning system. The low costs of production of the vital signs scanner can allow lower retail pricing and higher volume of sales, enabling an average consumer to afford the vital signs scanning system to personally scan and monitor trends of their vital signs for as an important part of preventive medical care of their own bodies.

Figure 9:
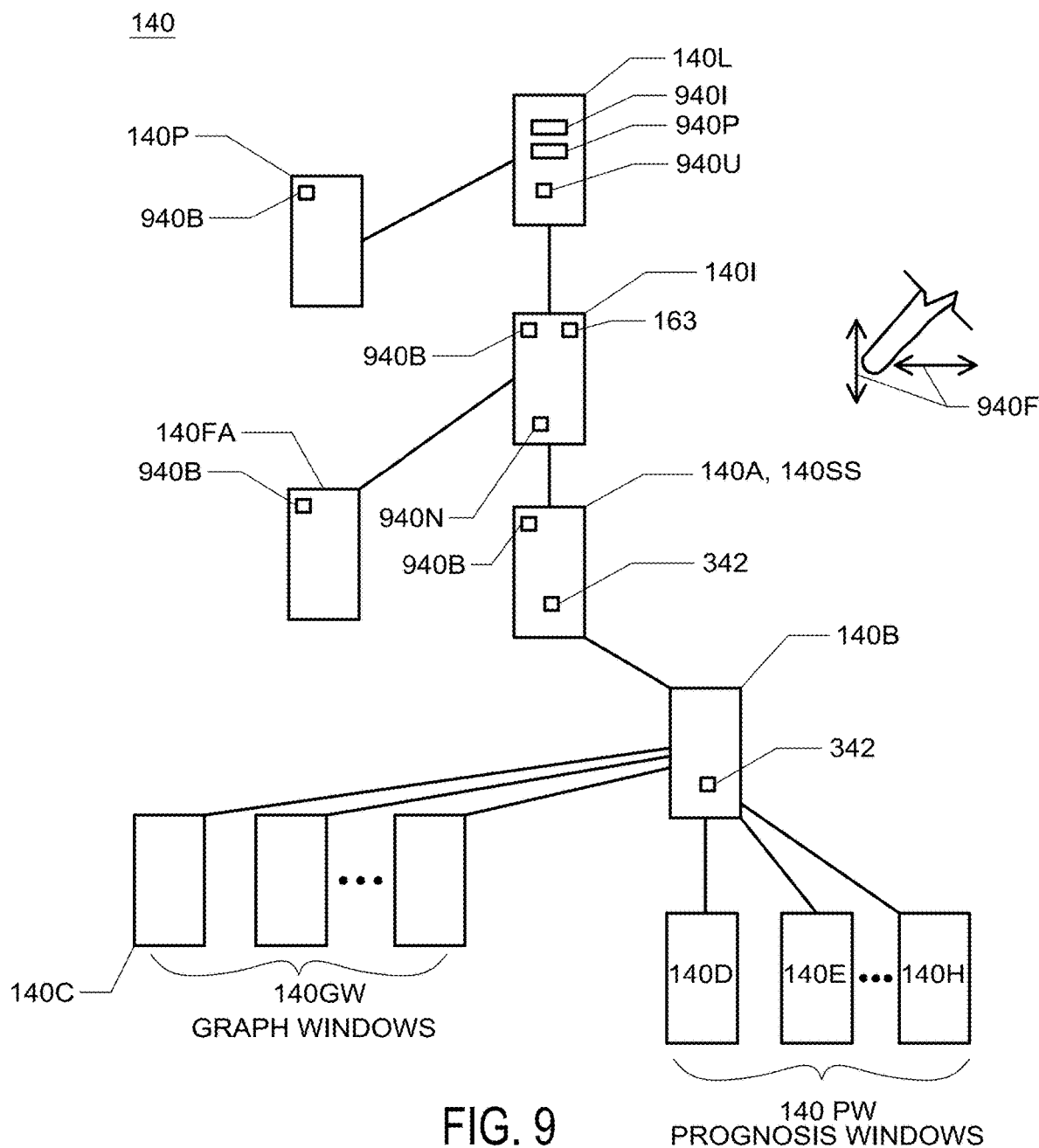
FIG. 9 illustrates an exemplary window hierarchy of the vital signs graphical user interface provided by the vital signs scanning software application executed by the personal wireless multifunction device.
Figure 10A:
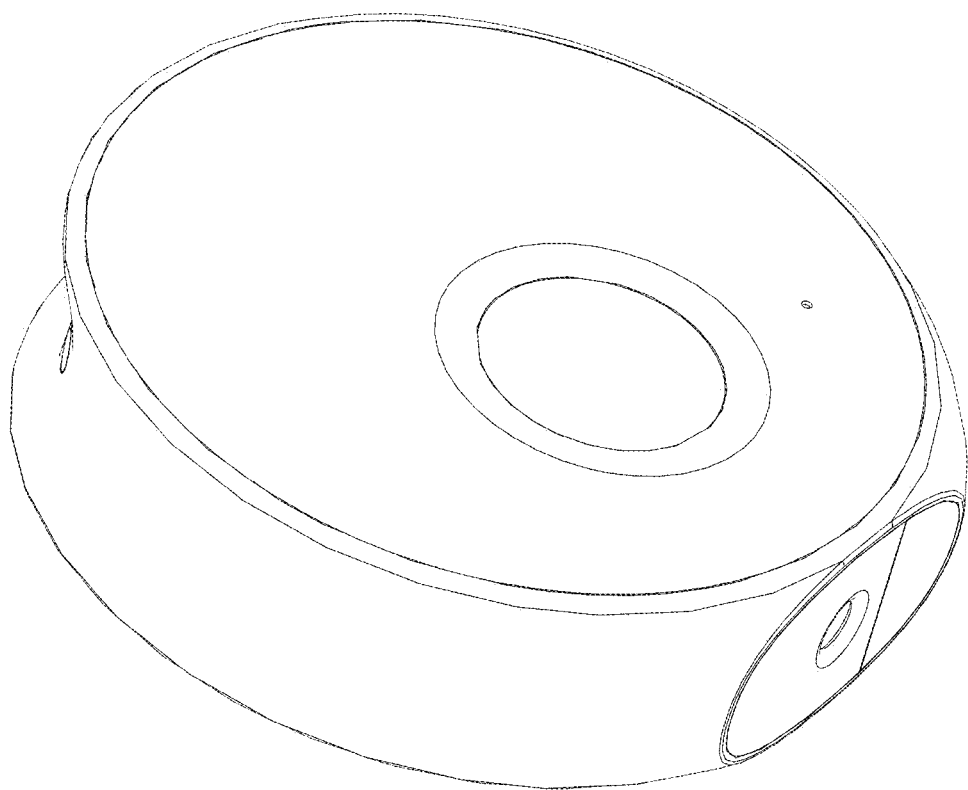
Figure 10B:
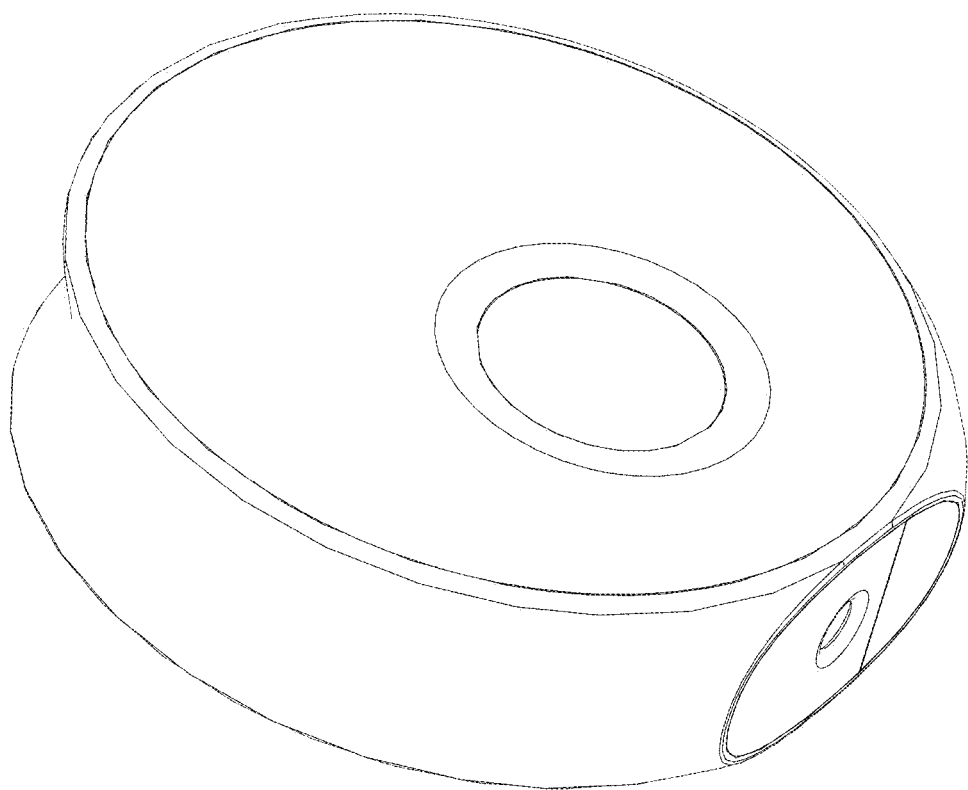
Figure 10C:
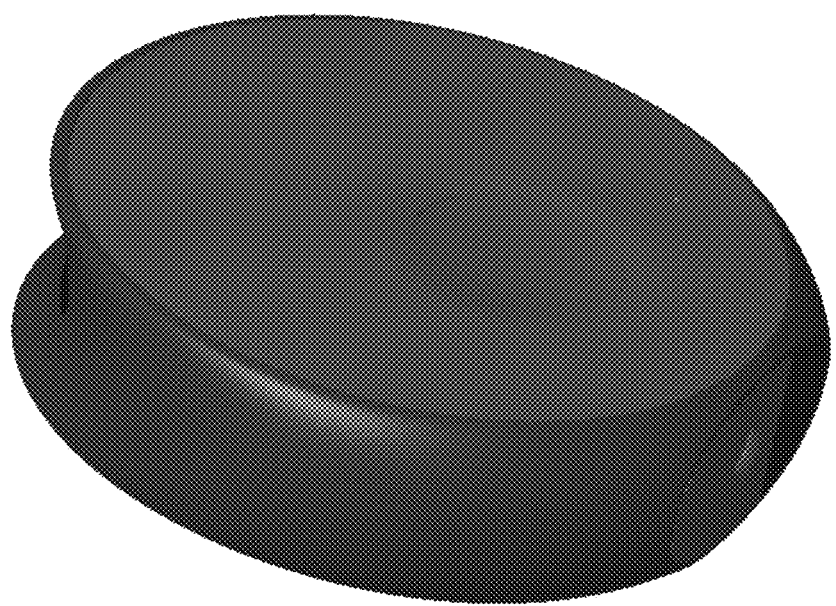
Figure 11A:
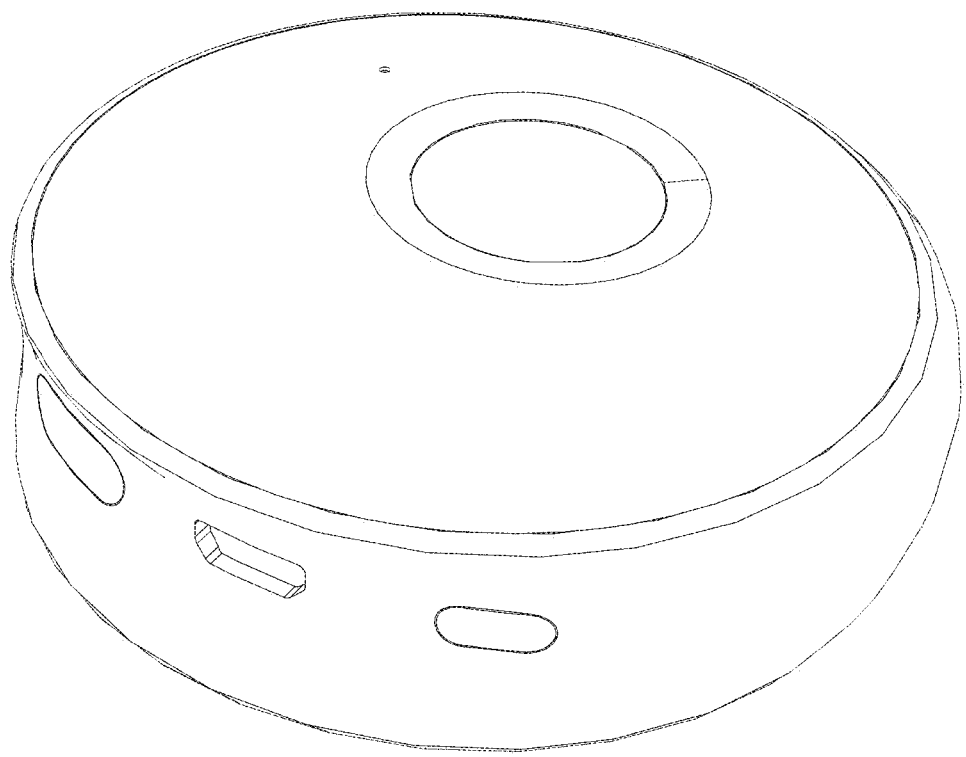
Figure 11B:
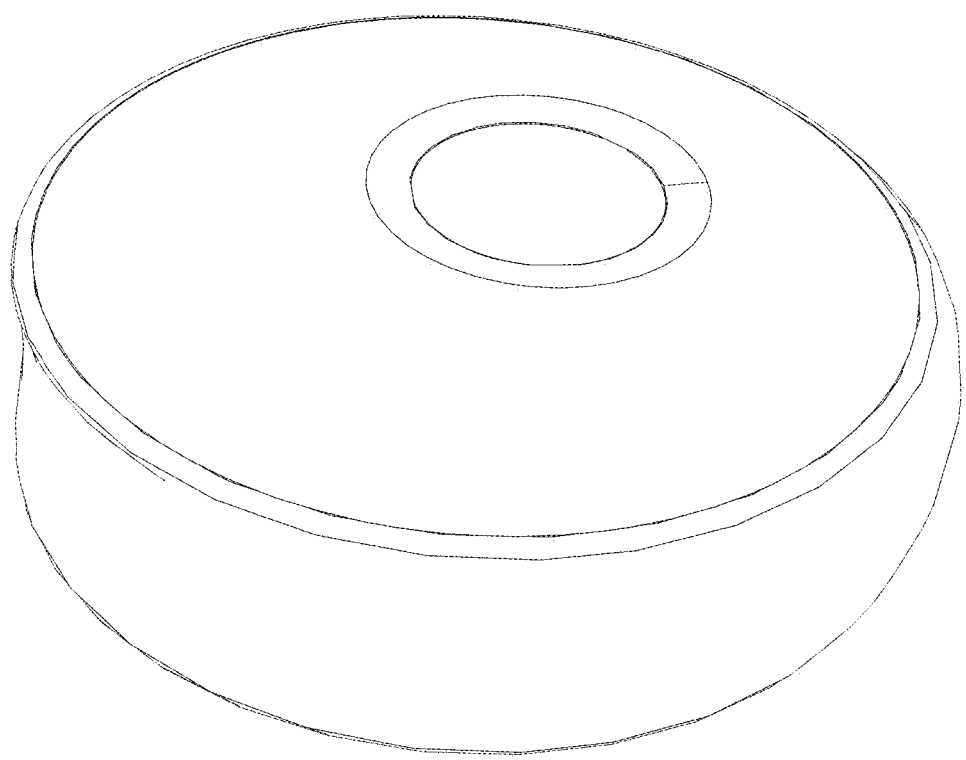
Figure 11C:
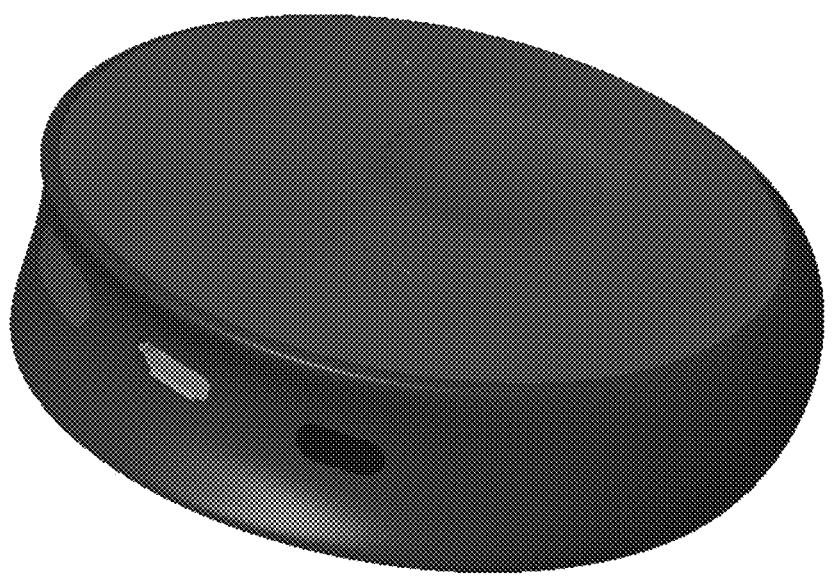
Figure 12A:
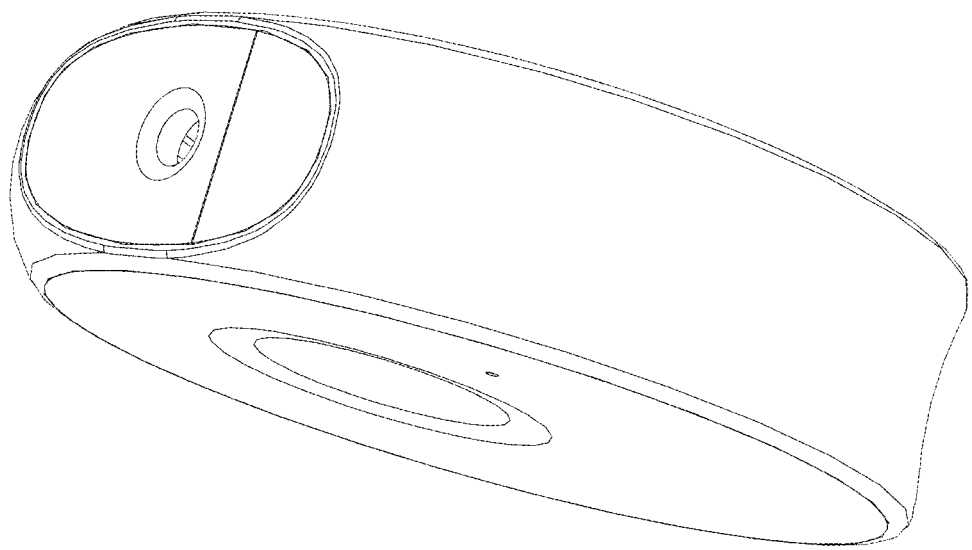
Figure 12B:
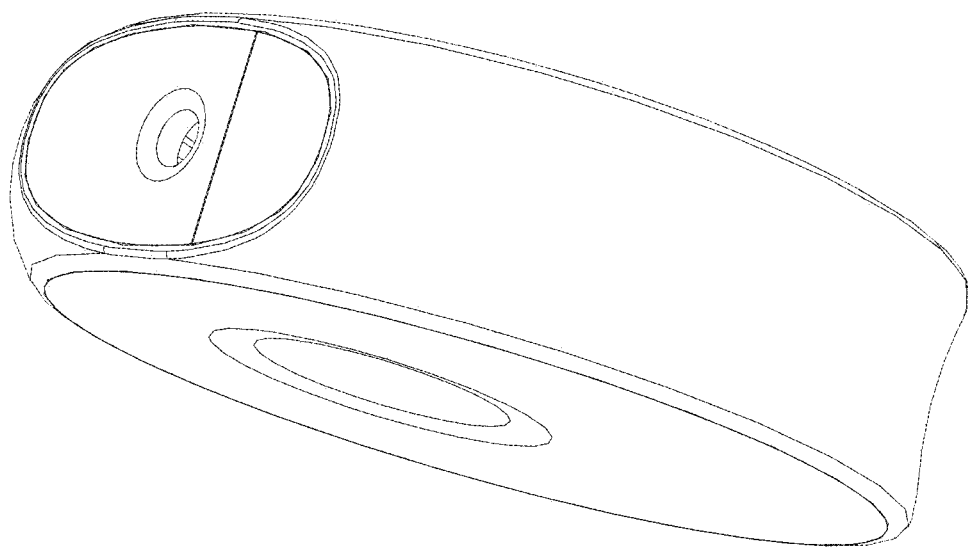
Figure 12C:
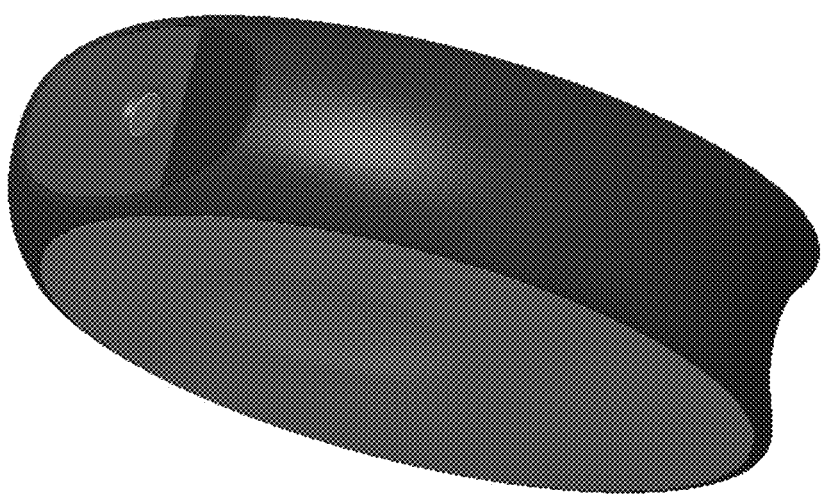
Figure 13A:
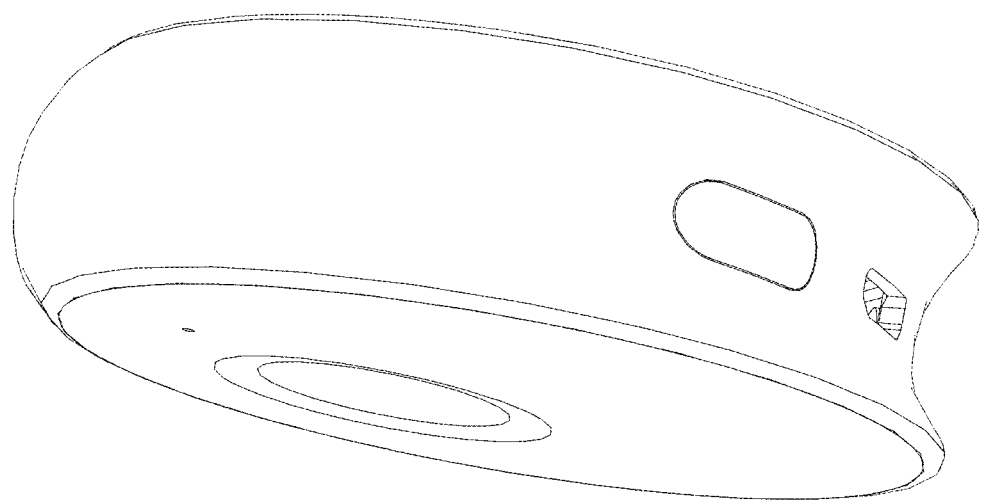
Figure 13B:
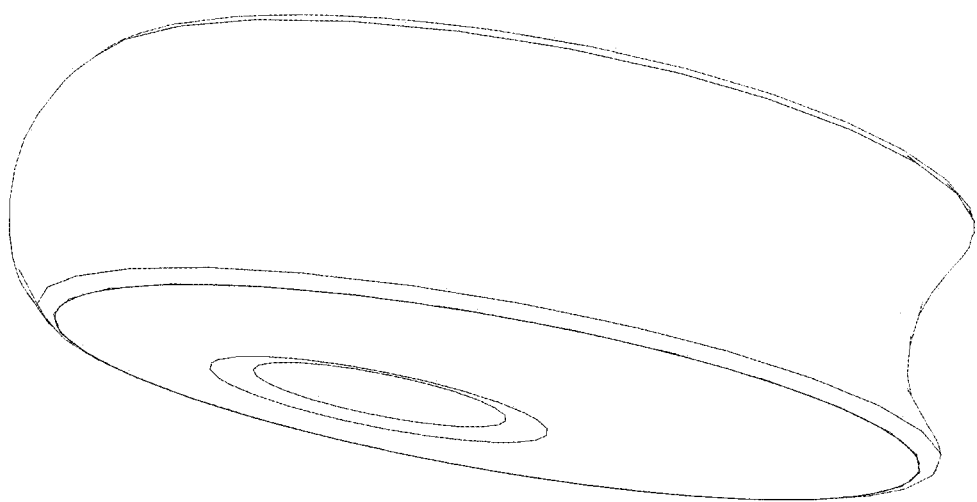
Figure 13C:
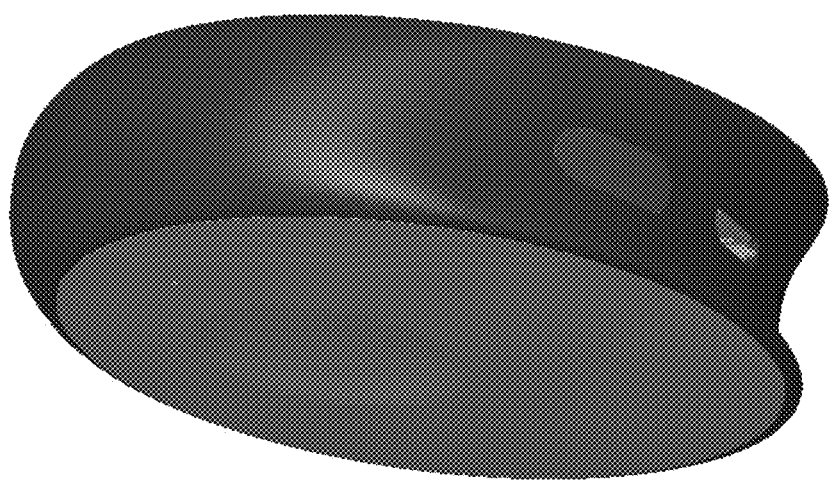
Figure 14A:
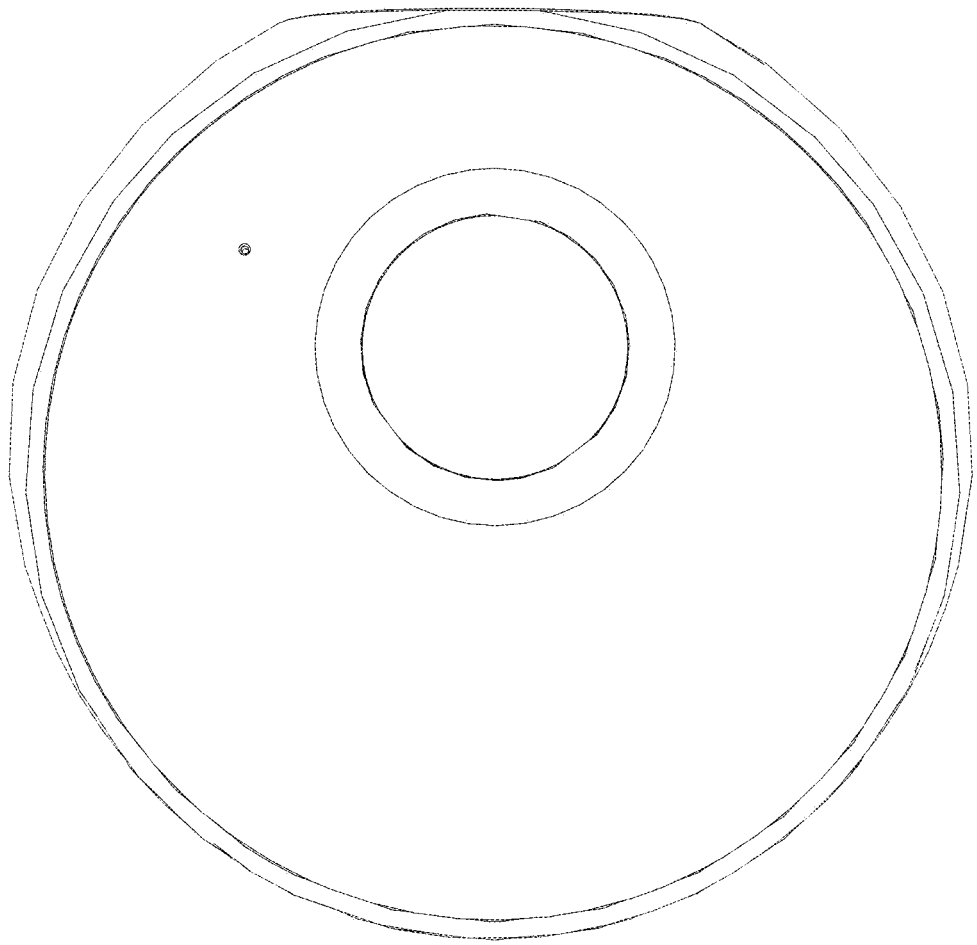
Figure 14B:
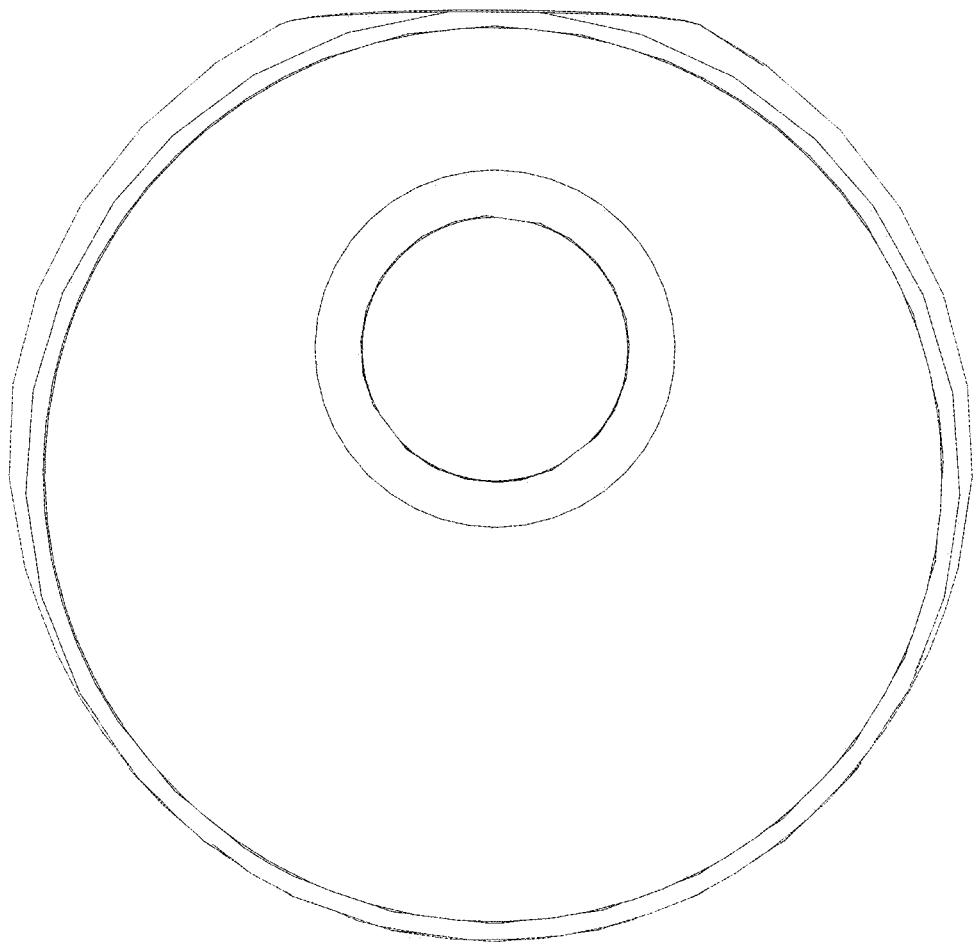
Figure 14C:
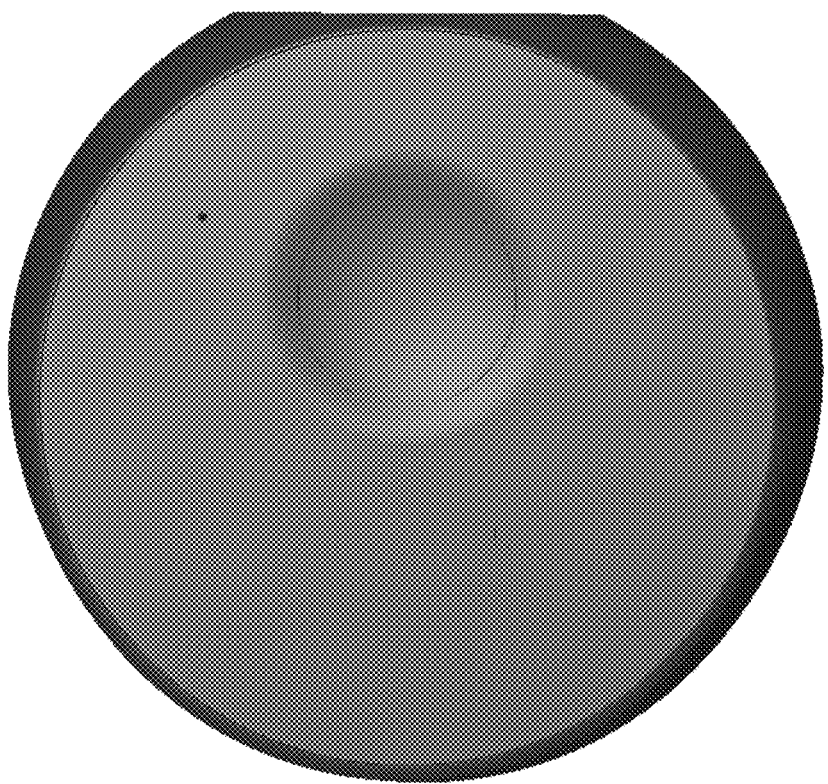
Figure 15A:
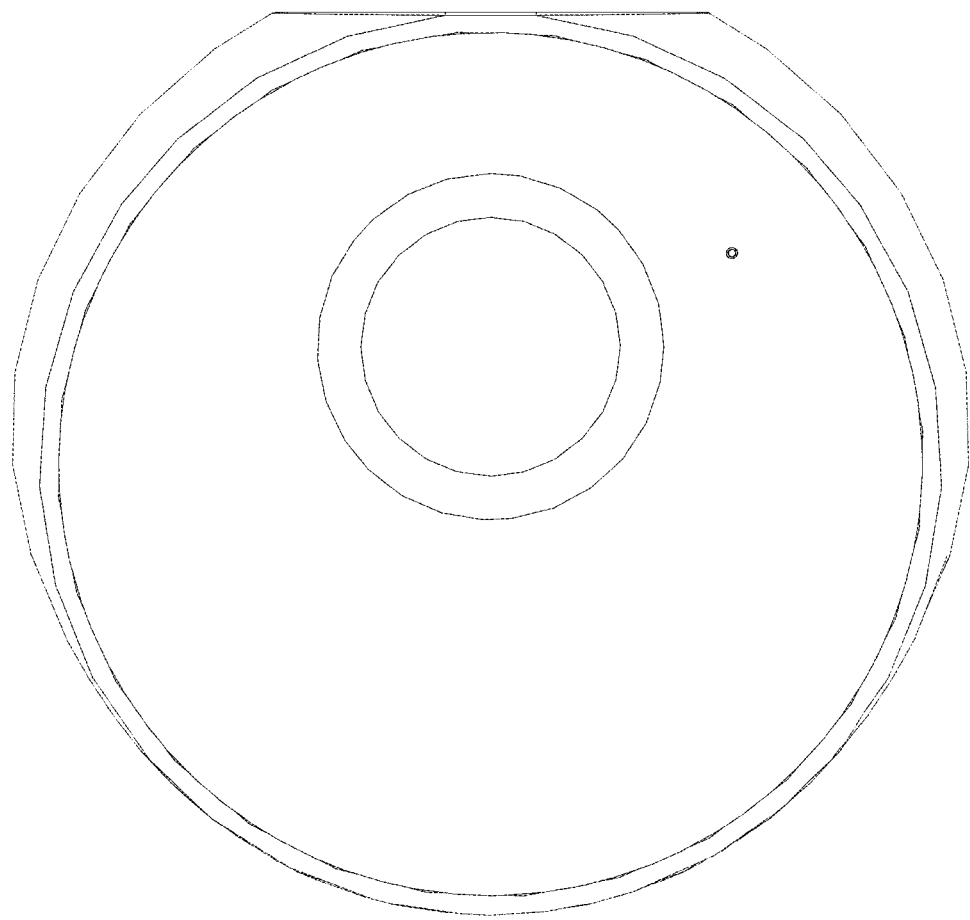
Figure 15B:
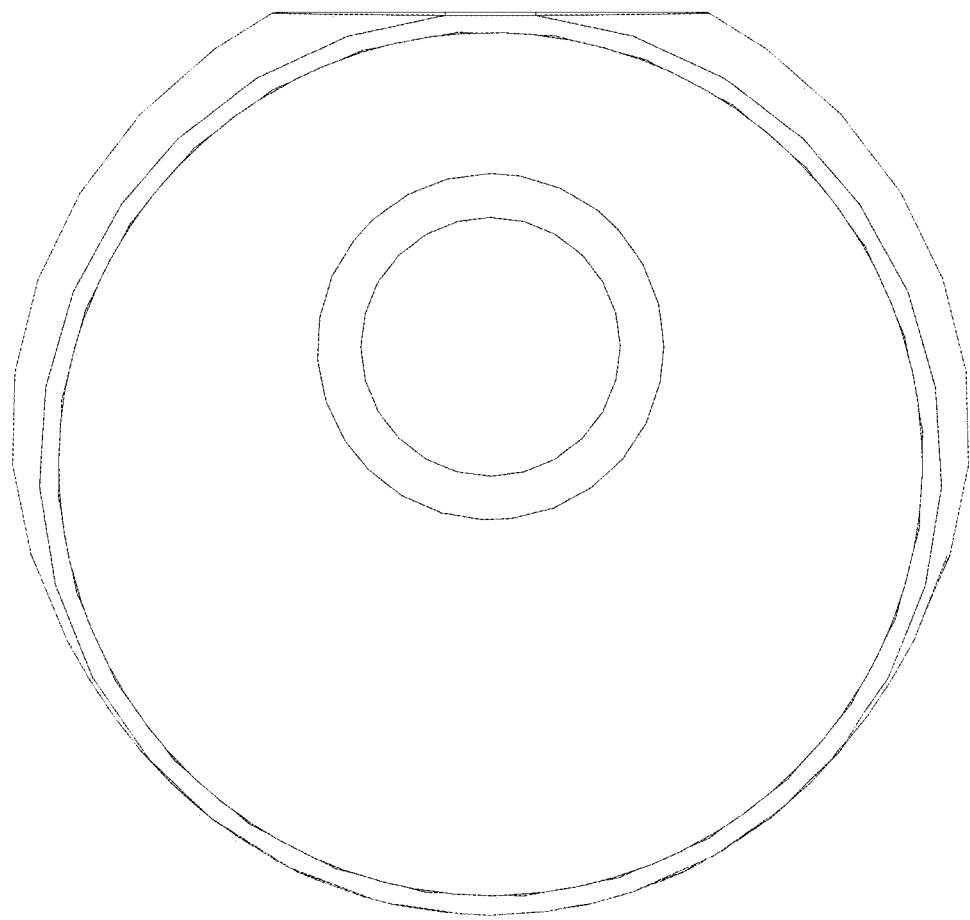
Figure 15C:
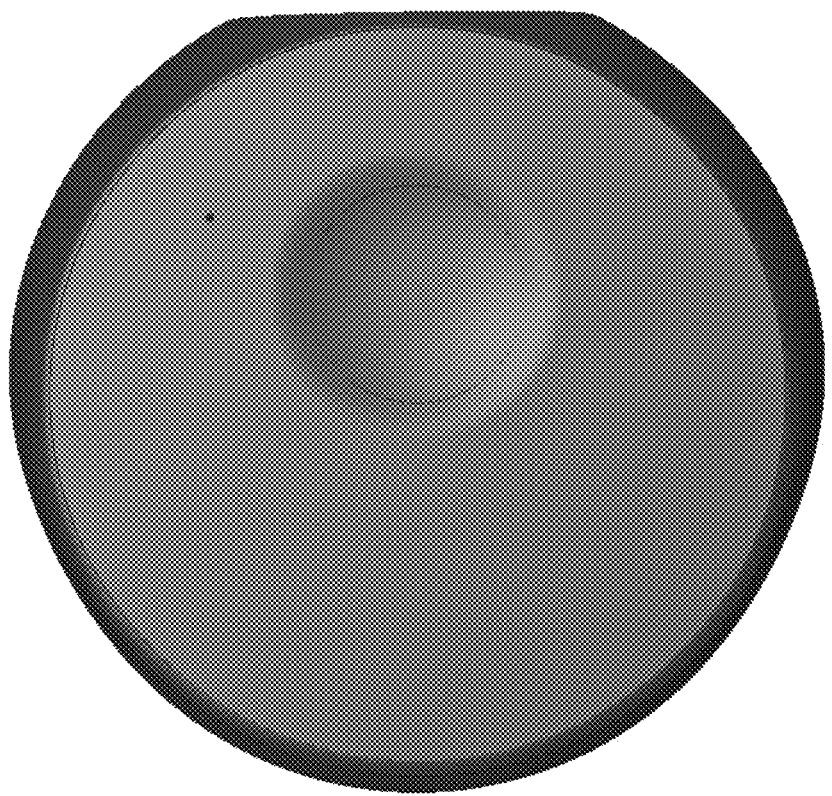
Figure 16A:
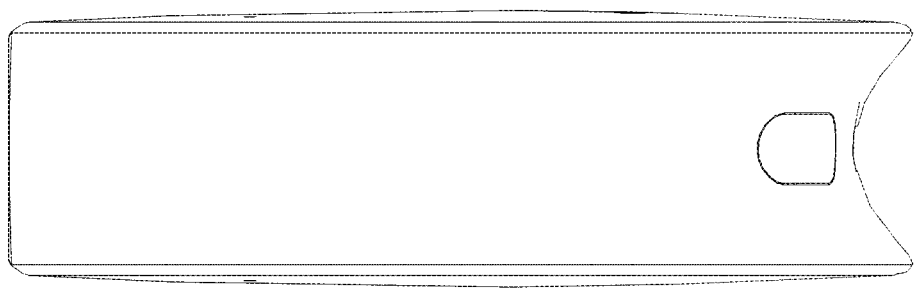
Figure 16B:
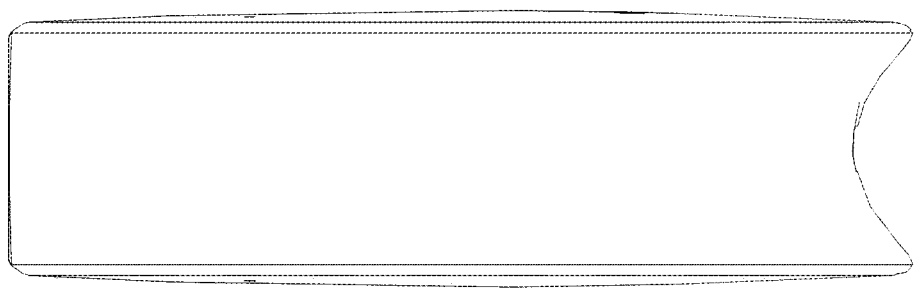
Figure 16C:
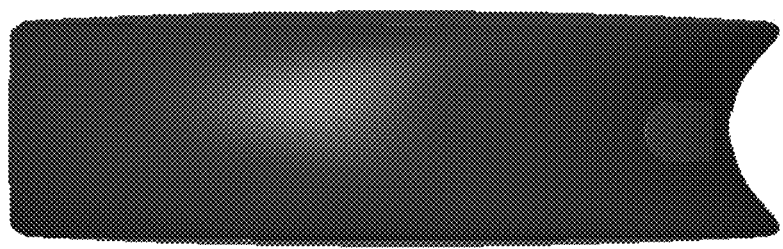
Figure 17A:
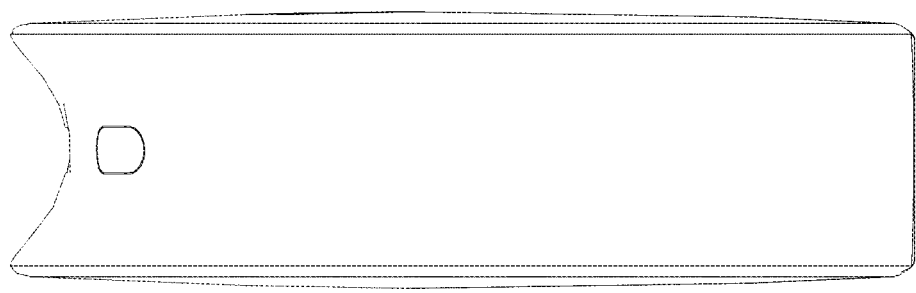
Figure 17B:
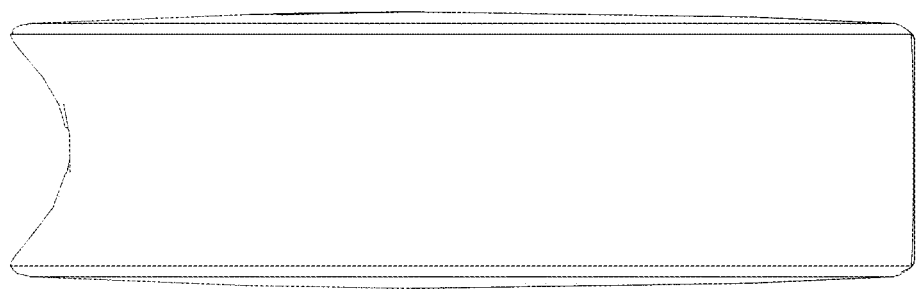
Figure 17C:
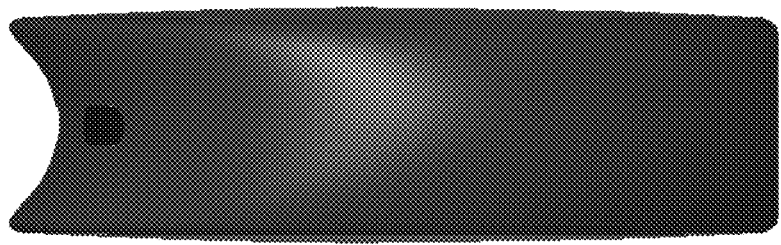
Figure 18A:
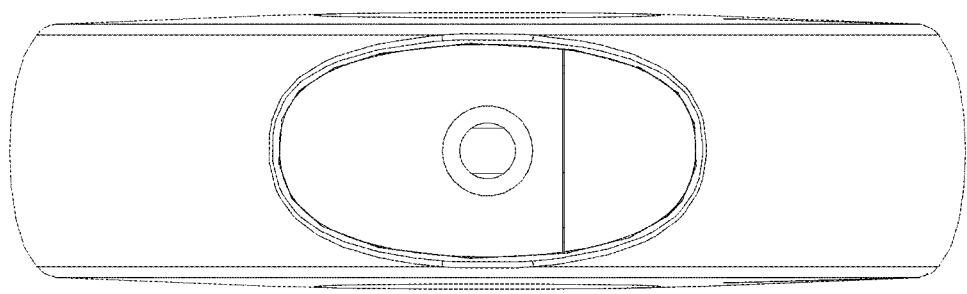
Figure 18B:
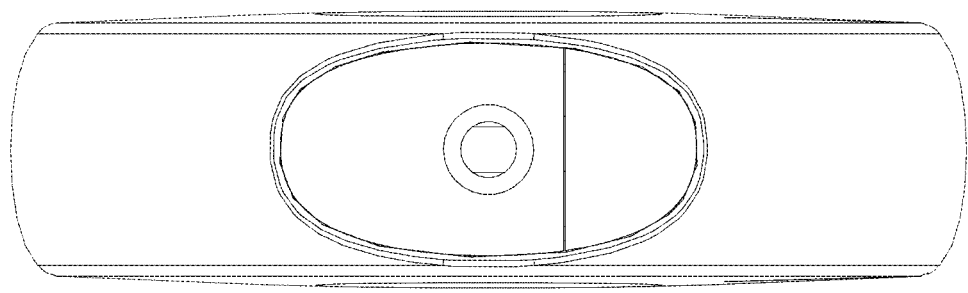
Figure 18C:
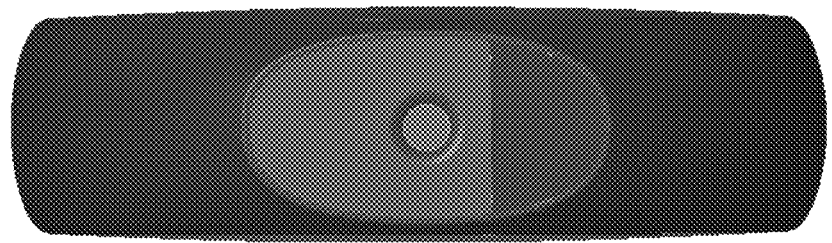
Figure 19A:
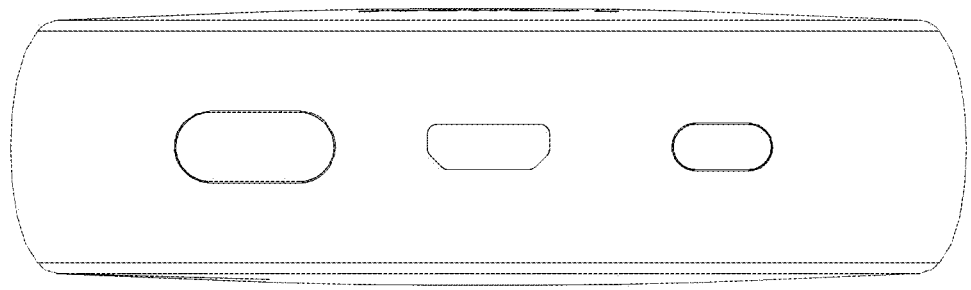
Figure 19B:
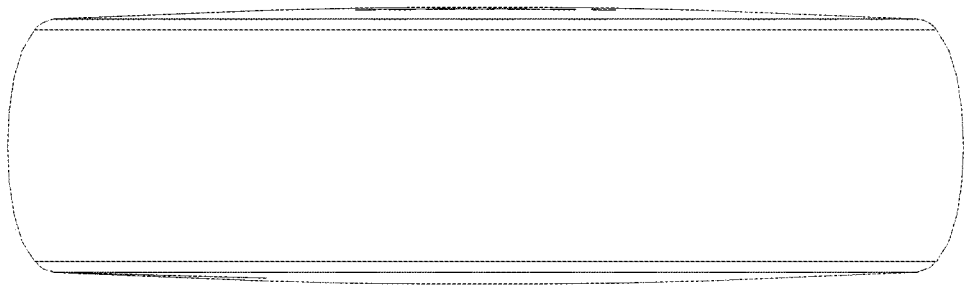
Figure 19C:
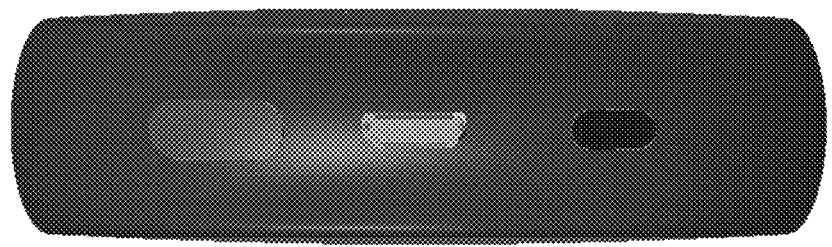

Referring now to FIG. 9, a diagram illustrating an exemplary hierarchy of windows provided by the scanning application software 140 is illustrated. A variety of scanning user interface windows of the scanning application software 140 have been described. The scanning application software 140 executed by a processor provides a user interface hierarchy of the scanning user interface windows. For example, a scanning login window 140L may be generated by the scanning application software 140 where a user inputs his login identification and password to gain access to personal vital signs scan data stored in the device 104. If the user is new, the login window 140L may have a new user button 940U that jumps to a profile window 140P that is displayed to the user. In the profile window 140P, the new user may input his login user ID 9401 and password 940P that he desires to use with the scanning software application to identify his personal vital signs scan data. Other information, such as sex, height, weight associated with a time and date may be entered by the user. As the days and/or years go by, the user may update this information in the profile so that the vital signs scanning system better knows what conditions might occur for the given user. The login and profile windows can also allow the scanning system to be shared with other users in a family. After logging in with user ID and password, the scanning system application may display the initial scanning window 140I.

Each of the windows of the vital signs scanning application may be navigated by pressing one or more virtual graphical buttons 940B,940N (e.g., back, next) and/or making one or more finger gestures 940F (e.g., up/down, left/right) dragged across a touch screen. A navigation bar may be provided with navigation buttons to navigate between selected windows. For example, pressing a scan button 161 in the initial window 140I displays the first scan window 140A. In the results window 140B or the second scan window 140SS, pressing a next scan button 342 causes the next scan to be performed by the scanner 102. Pressing another button in the initial window 140I takes a user to an add a note window 140FA to search and to add a note about a user's condition.

After scanning is completed, the scanning application software can automatically display the results window 140B. Additional buttons in the results window 140B may be used to navigate to various graph windows 140GW, such as the temperature graph window 140C shown in FIGS. 4A-4B. Additional buttons in the results window 140B may be used to navigate to various prognosis windows 140PW such as prognosis windows 140D-140H shown in FIGS. 5A-5B. In this manner, vital signs data and information can be displayed to the user in various ways.

The scanning software application 140 includes a number of instructions and routines that are executed by a personal wireless multifunction device 104. The personal wireless multifunction device 104 may include a smart phone, such as an APPLE IPHONE 5, IPHONE 4S, and SAMSUNG GALAXY S III for example, that support Bluetooth Smart. To help everyone use the device, assistive technology may be added to the scanning software application 140.

The significant software routines of the scanning software application 140 include a scan procedure controller based on scan quality algorithm, UI implementation, wide area network interfacing to cloud services, scan results interpretation, and trend charting.

CONCLUSION

Various specific materials, designs, dimensions, etc. are provided and are considered highly beneficial embodiments of the present disclosure in one regard. However, in other regard, such specifics are also merely illustrative of broader aspects of the present disclosure and should not be considered to necessarily limit to such broader aspects unless expressly specified to be required. In particular, the various specific dimensions provided as such examples are intended to be about any particular values provided, with typical tolerances and ranges of suitable alternatives as would be apparent to one of ordinary skill. Where particular combinations of such dimensions are provided for exemplary illustration of certain embodiments, the relative relationships between them are also contemplated as having been herein disclosed as additional beneficial aspects (even if the specific values of the relative dimensions change). For example, certain lengths, widths, and/or depths of particular components shown and described for a particular assembly provide overall geometries which may be varied by changing certain sub-sets of such dimensions, but may also be fixed relative to the ratios of these values despite the valued changing (so long as their general relationship remains). Similarly, such dimensions of different component parts also have similar relative relationships which are similarly contemplated, also as apparent to one of ordinary skill.

When implemented in software, the elements of the embodiments of the invention are essentially the code segments or instructions to perform the functional tasks described herein. The code segments or instructions are executable by a processor, such as processor 206,840, and can be stored in a storage device or a processor readable storage medium, such as memory 208,841, awaiting execution. The processor readable storage medium may include any medium that can store information. Examples of the processor readable storage medium include an electronic circuit, a semiconductor memory device, a read only memory (ROM), a flash memory, an erasable programmable read only memory (EPROM), a floppy diskette, a CD-ROM, an optical disk, a hard disk. The code segments or instructions may be downloaded via computer networks such as the Internet, Intranet, etc. into the processor readable storage medium.

Various combinations and sub-combinations, and modifications as may be made, of the presently disclosed components and embodiments and aspects are contemplated whether or not specifically disclosed hereunder, to the extent and as would be apparent to one of ordinary skill based upon review of this disclosure and in order to suit a particular intended purpose or application.

While certain embodiments of the disclosure have been described, these embodiments have been presented by way of example only, and are not intended to limit the scope of the disclosure. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by the claims that follow below.

What is claimed is:

1. A method of scanning vital signs data of a user, the method comprising:
   gripping a personal wireless vital signs scanner between first and second digits of the user's hand and connecting one of the first and second digits to a first electrode of the scanner;
   pressing a second electrode of the vital signs scanner against the user's forehead and forming a first circuit between the first and second electrodes through the user's body;
   activating a first scan of the vital signs scanner on a portable wireless multifunction device wirelessly connected to the vital signs scanner;
   in response to activating the first scan, collecting a first set of vital signs data from the user's forehead using the vital signs scanner;
   after collecting the first set of vital signs data, selecting to perform a second scan using the vital signs scanner on the multifunction device;
   after selecting to perform the second scan, moving the vital signs scanner from the user's forehead and pressing the second electrode of the vital signs scanner against a different portion of the user's body and forming a second circuit between the first and second electrodes through the user's body, wherein the different portion of the user's body is different from the forehead, the first digit, and the second digit;
   activating the second scan of the vital signs scanner on the multifunction device;
   in response to activating the second scan, collecting a second set of vital signs data from the different portion of the user's body using the vital signs scanner;
   transmitting the collected first and second sets of vital sign data to the multifunction device; and
   displaying a portion of the collected first and second sets of vital signs data to the user on a display of the multifunction device.

2. The method of claim 1, wherein collecting the first set of vital signs data includes collecting data for a first time period, and collecting the second set of vital signs data includes collecting data from a second time period, and wherein, the first period of time is between one and ten seconds, and the second period of time is between ten and thirty seconds.

3. The method of claim 1, wherein
pressing the second electrode of the vital signs scanner against the user's forehead includes
contacting at least one light emitting diode (LED) and at least one photodiode of the vital signs scanner near the user's forehead, wherein the at least one light emitting diode is configured to radiate an LED light onto the user's forehead and the photodiode is configured to receive a reflected LED light from the user's forehead and generate a signal used to obtain a measure of pulse oximetry.

4. The method of claim 3, further comprising
shading the at least one photodiode from the at least one light emitting diode (LED) to avoid directed light therefrom impinging on the photodiode.

5. The method of claim 1, wherein
the different portion of the user's body is the user's chest.

6. The method of claim 1, wherein gripping the vital signs scanner between first and second digits of the user's hand includes gripping the vital signs scanner between a thumb and a forefinger of the user's left hand.

7. The method of claim 1, further including using microphones in the vital signs scanner to record body sounds of the user.

8. The method of claim 1, wherein the portable wireless multifunction device is one of a smart phone, a tablet computer, or a portable music player.

9. The method of claim 1, wherein activating the second scan of the vital signs scanner on the multifunction device includes activating the first or second scan using a user interface button of a software application in the multifunction device.

10. The method of claim 1, wherein the collected first or second set of vital signs data includes at least one of ECG, heart rate, breathing rate, temperature, blood pressure, or blood oxygenation.

* * * * *